United States Patent
Iwasaki et al.

(10) Patent No.: US 11,432,742 B2
(45) Date of Patent: Sep. 6, 2022

(54) AIRWAY VENTILATION STATE CALIBRATION SYSTEM AND SYSTEM FOR PREDICTING AIRWAY DEFORMATION DURING SLEEP

(71) Applicant: Kagoshima University, Kagoshima (JP)

(72) Inventors: Tomonori Iwasaki, Kagoshima (JP); Youichi Yamasaki, Kagoshima (JP)

(73) Assignee: KAGOSHIMA UNIVERSITY, Kogoshima (JP)

( * ) Notice: Subject to any disclaimer, the term of this patent is extended or adjusted under 35 U.S.C. 154(b) by 562 days.

(21) Appl. No.: 16/489,311

(22) PCT Filed: Mar. 1, 2018

(86) PCT No.: PCT/JP2018/007780
§ 371 (c)(1),
(2) Date: Aug. 27, 2019

(87) PCT Pub. No.: WO2018/159759
PCT Pub. Date: Sep. 7, 2018

(65) Prior Publication Data
US 2020/0060579 A1 Feb. 27, 2020

(30) Foreign Application Priority Data
Mar. 1, 2017 (JP) .............................. JP2017-038358

(51) Int. Cl.
*A61B 5/085* (2006.01)
*G16H 50/50* (2018.01)
(Continued)

(52) U.S. Cl.
CPC ................ *A61B 5/085* (2013.01); *A61B 6/03* (2013.01); *G06T 7/0012* (2013.01); *G06T 17/00* (2013.01); *G16H 50/50* (2018.01); *A61B 5/055* (2013.01)

(58) Field of Classification Search
CPC .................. G06T 17/00; G06T 7/0012; A61B 2560/0223; A61B 5/055; A61B 5/085;
(Continued)

(56) References Cited

U.S. PATENT DOCUMENTS

2011/0293156 A1* 12/2011 Hsiao ........................ G06T 7/62
382/128

FOREIGN PATENT DOCUMENTS

WO    2006/037627 A2    4/2006
WO    2012/035538 A1    3/2012
(Continued)

OTHER PUBLICATIONS

Iwasaki et al, "Evaluation of upper airway obstruction in Class II children with fluid-mechanical simulation", [online], Feb. 2011, vol. 139, Issue 2, e135-e145, American Journal of Orthodontics and Dentofacial Orthopedics.
(Continued)

*Primary Examiner* — Manuchehr Rahmjoo
(74) *Attorney, Agent, or Firm* — K&L Gates LLP; Louis C. Cullman; Dennis A Majewski

(57) ABSTRACT

A nasal-cavity model generator (41) extracts pixels having pixel density values within a specific range from three-dimensional image data on a nasal cavity of a subject contained in DICOM data (21), and generates a nasal cavity model (50), which is a three-dimensional model of the nasal cavity, based on three-dimensional image data composed of the extracted pixels. A nasal-cavity resistance calculator (42) calculates a nasal cavity resistance (51) through fluid analy-
(Continued)

sis using the nasal cavity model (50) generated by the nasal-cavity model generator (41). An adjuster (43) adjusts the specific range of the pixel density values of the pixels to be extracted for generation of the nasal cavity model (50) by the nasal-cavity model generator (41) such that the nasal cavity resistance (51) calculated by the nasal-cavity resistance calculator (42) is equal to a nasal cavity resistance (52) actually measured with a nasal-cavity draft gauge.

10 Claims, 30 Drawing Sheets

(51) Int. Cl.
*A61B 6/03* (2006.01)
*G06T 7/00* (2017.01)
*G06T 17/00* (2006.01)
*A61B 5/055* (2006.01)

(58) Field of Classification Search
CPC ... A61B 5/1075; A61B 5/6819; A61B 5/7275; A61B 6/03; A61B 6/032; A61B 6/466; A61B 6/5217; A61B 8/483; A61B 8/5223; G16H 20/40; G16H 30/20; G16H 30/40; G16H 50/30; G16H 50/50
See application file for complete search history.

(56) References Cited

FOREIGN PATENT DOCUMENTS

| | | |
|---|---|---|
| WO | 2016/006633 A1 | 1/2016 |
| WO | 2018/159759 A1 | 9/2018 |

OTHER PUBLICATIONS

International Search Report and Written Opinion for International Patent Application Serial No. PCT/JP2018/007780 dated May 29, 2018.

* cited by examiner

CT VALUE  −1000∼−200 Hu   −1000∼−300 Hu   −1000∼−400 Hu
  (A)          (B)              (C)              (D)

FIG.10

| R1−R2(Pa/ml/s) | AMOUNT OF INCREMENT/DECREMENT OF CT2(Hu) |
|---|---|
| +0.5~ | +100 |
| +0.3~+0.5 | +50 |
| +0.1~+0.3 | +20 |
| +0.05~+0.1 | +10 |
| −0.05~0.05 | EQUAL |
| −0.1~−0.05 | −10 |
| −0.3~−0.1 | −20 |
| −0.5~−0.3 | −50 |
| ~−0.5 | −100 |

(A)　　　(B)

AIRWAY VENTILATION STATE CALIBRATION SYSTEM AND SYSTEM FOR PREDICTING AIRWAY DEFORMATION DURING SLEEP

PRIORITY CLAIM

This application is a national phase entry of PCT/JP2018/00/780, filed on Mar. 1, 2018, which claims priority to Japanese Patent Application No. 2017-038358, filed on Mar. 1, 2017, the entire disclosures of which are incorporated by reference herein.

TECHNICAL FIELD

The present disclosure relates to an airway-ventilation-state calibration system and a system for predicting airway deformation in a sleeping state.

BACKGROUND ART

Obstructive sleep apnea syndrome (OSAS) is a respiratory disease that causes obstruction of the upper airway of a patient and leads to respiratory disorder in a sleeping state, thereby providing various adverse effects on the whole body. Most attention has focused on the obstructive sleep apnea syndrome (hereinafter simply referred to as "sleep apnea syndrome") as a cause of serious traffic accidents because the patient gets excessively sleepy during the daytime due to insufficient night sleep.

Some diagnostic methods for sleep apnea syndrome have been suggested. For example, Non Patent Literature 1 discloses a method of diagnosing sleep apnea syndrome by constructing a fluid model inside an upper airway on a computer on the basis of a three-dimensional CT image and executing fluid analysis using the constructed fluid model. This method can narrow down candidate sites that obstruct the ventilation to some extent, on the basis of a pressure distribution inside the upper airway and a distribution of air flow velocity.

The rate of developing sleep apnea syndrome is reported to be 4% for adults and 2% for children regardless of their ages from childhood to puberty. Although the sleep apnea syndrome occurs at such a relatively high rate, no effective method has been established for specifying a site responsible for sleep apnea syndrome and providing a sufficient therapeutic outcome. The above-mentioned method disclosed in Non Patent Literature 1 is one of the few effective methods for narrowing down candidate sites responsible for sleep apnea syndrome, but cannot always provide an effective therapeutic outcome because of the following disadvantages:

(1) The upper airway is simulated as a non-deformable rigid model. This model cannot achieve fluid analysis in view of elastic deformation of the upper airway and thus cannot simulate obstruction of the upper airway.

(2) Only the upper airway is modeled without modeling of the tissues surrounding the upper airway, which are often fundamentally responsible for sleep apnea syndrome. This model fails in simulation of deformation of the tissues surrounding the upper airway. The model thus requires a diagnostic technician to indirectly guess a fundamentally responsible site from the results of fluid analysis.

For example, the most typical site that causes sleep apnea syndrome is a narrowed portion in the upper airway caused by the tongue hanging down due to the gravity when a patient lies in a supine position. Unfortunately, the technique disclosed in Non Patent Literature 1 does not involve modeling of the tongue, which is one of the tissues surrounding the upper airway, and fails to simulate a narrowed portion in the upper airway caused by the tongue hanging down due to the gravity. This technique thus cannot achieve ready specification of a narrowed portion in the upper airway caused by the tongue hanging down due to the gravity in the supine position as the cause of sleep apnea syndrome.

(3) The air is assumed to flow in one direction inside the upper airway in the fluid analysis using the simulation model, in contrast to the air flow in two directions in the actual respiration (the air flow periodically varying between during exhalation and inhalation). The model thus cannot simulate the fluid flow inside the upper airway in accordance with the actual respiration.

For example, Patent Literature 1 discloses a diagnostic device, a diagnostic system, a diagnostic method, and a program that can more certainly provide a preferable therapeutic outcome for respiratory diseases.

CITATION LIST

Patent Literature

Patent Literature 1: International Publication No. WO 2016/006633

Non Patent Literature

Non Patent Literature 1: Iwasaki et al., "Evaluation of upper airway obstruction in Class II children with fluid-mechanical simulation", [online], February 2011, Vol. 139, Issue 2, American Journal of Orthodontics and Dentofacial Orthopedics

SUMMARY OF INVENTION

Technical Problem

The above-mentioned diagnosis requires an airway model to exactly simulate the actual airway. Unfortunately, practically no means has been provided that can determine whether a generated airway model exactly simulates the actual airway.

Different patients of obstructive sleep apnea syndrome (OSAS) have various responsible sites in the upper airways. These responsible sites require different treatment procedures for OSAS. The responsible site should therefore be specified in the first step of the treatment. In an exemplary existing method for specifying a responsible site, the condition of the upper airway of a subject is observed with X-rays, CT (magnetic resonance imaging (MRI)), or an endoscope. Unfortunately, the results of such observation do not contribute to ready specification of a site responsible for OSAS because the condition of the upper airway varies between a waking state and a sleeping state.

An objective of the disclosure, which has been accomplished in view of the above situation, is to provide a model generating device, model generating method, and a program that can construct a nasal cavity model that exactly simulates a nasal cavity of a subject.

Another objective of the disclosure, which has been accomplished in view of the above situation, is to provide a system for predicting airway deformation in a sleeping state, a method for predicting airway deformation in a sleeping state, and a program that can exactly specify a site responsible for sleep apnea syndrome.

Solution to Problem

In order to achieve the above objective, a model generating device according to a first aspect of the disclosure includes: a nasal-cavity model generator configured to extract pixels having pixel density values within a specific range from three-dimensional image data on a nasal cavity of a subject, and generate a nasal cavity model based on three-dimensional image data composed of the extracted pixels, the nasal cavity model being a three-dimensional model of the nasal cavity; a nasal-cavity resistance calculator configured to calculate a nasal cavity resistance through fluid analysis using the nasal cavity model generated by the nasal-cavity model generator; and an adjuster configured to adjust the specific range of the pixel density values of the pixels to be extracted for generation of the nasal cavity model by the nasal-cavity model generator such that the nasal cavity resistance calculated by the nasal-cavity resistance calculator is equal to an actually-measured nasal cavity resistance.

In this configuration, the nasal-cavity model generator may generate the nasal cavity model based on the pixels having pixel density values within a range defined between a first pixel density value and a second pixel density value larger than the first pixel density value, the first pixel density value being approximate to a pixel density value of the air, and the adjuster may adjust the second pixel density value such that the nasal cavity resistance calculated by the nasal-cavity resistance calculator is equal to the actually-measured nasal cavity resistance.

The adjuster may increment the second pixel density value if the nasal cavity resistance calculated by the nasal-cavity resistance calculator is larger than the actually-measured nasal cavity resistance, and decrement the second pixel density value if the nasal cavity resistance calculated by the nasal-cavity resistance calculator is smaller than the actually-measured nasal cavity resistance.

The adjuster may decrease an amount of increment or decrement of the second pixel density value as the nasal cavity resistance calculated by the nasal-cavity resistance calculator approaches the actually-measured nasal cavity resistance.

The model generating device may further include an upper-airway model generator configured to extract pixels from three-dimensional image data on a maxillofacial area of the subject and generate a three-dimensional model of a tissue of an upper airway based on three-dimensional image data composed of the extracted pixels, the pixels having the pixel density values within the specific range adjusted by the adjuster.

A model generating method according to a second aspect of the disclosure involves: a nasal-cavity model generation step of extracting pixels having pixel density values within a specific range from three-dimensional image data on a nasal cavity of a subject, and generating a nasal cavity model based on three-dimensional image data composed of the extracted pixels, the nasal cavity model being a three-dimensional model of the nasal cavity; a simulation step of calculating a nasal cavity resistance through fluid analysis using the nasal cavity model generated in the nasal-cavity model generation step; and an adjustment step of adjusting the specific range of the pixel density values of the pixels to be extracted for generation of the nasal cavity model in the nasal-cavity model generation step until the nasal cavity resistance calculated in the simulation step becomes equal to a nasal cavity resistance actually measured with a nasal-cavity draft gauge.

A program according to a third aspect of the disclosure causes a computer to function as: a nasal-cavity model generator configured to extract pixels having pixel density values within a specific range from three-dimensional image data on a nasal cavity of a subject, and generate a nasal cavity model based on three-dimensional image data composed of the extracted pixels, the nasal cavity model being a three-dimensional model of the nasal cavity; a nasal-cavity resistance calculator configured to calculate a nasal cavity resistance through fluid analysis using the nasal cavity model generated by the nasal-cavity model generator; and an adjuster configured to adjust the specific range of the pixel density values of the pixels to be extracted for generation of the nasal cavity model by the nasal-cavity model generator such that the nasal cavity resistance calculated by the nasal-cavity resistance calculator is equal to a nasal cavity resistance actually measured with a nasal-cavity draft gauge.

A system for predicting airway deformation in a sleeping state according to a fourth aspect of the disclosure includes: the model generating device according to the first aspect of the disclosure; a conversion equation generator configured to generate conversion equations by an optimization procedure using three-dimensional models of upper airways of a plurality of subjects in waking states and three-dimensional models of the upper airways of a plurality of subjects in sleeping states, the conversion equations converting location information on a specific site of an upper airway in a waking state into location information on the specific site in a sleeping state; and an estimator configured to estimate location information on the specific site of the upper airway of the subject in a sleeping state by assigning location information on the specific site of the upper airway of the subject in a waking state to the generated conversion equations.

In this configuration, the conversion equation generator may generate coefficients of the conversion equations through regression analysis using location information on specific sites of the upper airways of the subjects in waking states obtained from the three-dimensional models of the upper airways in waking states and location information on the specific sites in sleeping states obtained from the three-dimensional models of the upper airways in sleeping states.

The conversion equations may be linear combination equations containing terms of position coordinates of the specific site of the upper airway in a waking state and terms of a pressure applied to the specific site, the pressure being obtained through fluid analysis using a three-dimensional model of the upper airway in a sleeping state.

The conversion equations may be linear combination equations further containing terms of an apnea hypopnea index.

The conversion equations may be linear combination equations further containing terms of an index related to the level of obesity of the subject.

A method for predicting airway deformation in a sleeping state according to a fifth aspect of the disclosure involves: a nasal-cavity model generation step of extracting pixels having pixel density values within a specific range from three-dimensional image data on a nasal cavity of a subject, and generating a nasal cavity model based on three-dimensional image data composed of the extracted pixels, the nasal cavity model being a three-dimensional model of the nasal cavity; a simulation step of calculating a nasal cavity resistance through fluid analysis using the nasal cavity model generated in the nasal-cavity model generation step; an adjustment step of adjusting the specific range of the pixel density values of the pixels to be extracted for generation of the nasal cavity model in the nasal-cavity model generation step until the nasal cavity resistance calculated in the simulation step becomes equal to a nasal cavity resistance actually measured with a nasal-cavity draft gauge; a conversion equation generation step of generating conversion equations by an optimization procedure using three-dimensional models of upper airways of a plurality of subjects in waking states and three-dimensional models of the upper airways of a plurality of subjects in sleeping states, the conversion equations converting location information on a specific site of an upper airway in a waking state into location information on the specific site in a sleeping state; and an estimation step of estimating location information on the specific site of the upper airway of the subject in a sleeping state by assigning location information on the specific site of the upper airway of the subject in a waking state to the generated conversion equations.

A program according to a sixth aspect of the disclosure causes a computer to function as: a nasal-cavity model generator configured to extract pixels having pixel density values within a specific range from three-dimensional image data on a nasal cavity of a subject, and generate a nasal cavity model based on three-dimensional image data composed of the extracted pixels, the nasal cavity model being a three-dimensional model of the nasal cavity; a nasal-cavity resistance calculator configured to calculate a nasal cavity resistance through fluid analysis using the nasal cavity model generated by the nasal-cavity model generator; an adjuster configured to adjust the specific range of the pixel density values of the pixels to be extracted for generation of the nasal cavity model by the nasal-cavity model generator such that the nasal cavity resistance calculated by the nasal-cavity resistance calculator is equal to a nasal cavity resistance actually measured with a nasal-cavity draft gauge; a conversion equation generator configured to generate conversion equations by an optimization procedure using three-dimensional models of upper airways of a plurality of subjects in waking states and three-dimensional models of the upper airways of a plurality of subjects in sleeping states, the conversion equations converting location information on a specific site of an upper airway in a waking state into location information on the specific site in a sleeping state; and an estimator configured to estimate location information on the specific site of the upper airway of the subject in a sleeping state by assigning location information on the specific site of the upper airway of the subject in a waking state to the generated conversion equations.

Advantageous Effects of Invention

The disclosure contributes to generation of a nasal cavity model of which the nasal cavity resistance is equal to the actually-measured resistance and can thus achieve construction of a nasal cavity model that exactly simulates a nasal cavity of the subject.

Furthermore, the disclosure contributes to statistical prediction of a three-dimensional model of the upper airway of each subject in a sleeping state from a three-dimensional model of the upper airway of the subject in a waking state, using three-dimensional models of upper airways of a plurality of subjects in waking states and three-dimensional models of the upper airways of a plurality of subjects in sleeping states. The disclosure can thus determine the shape of the upper airway in a sleeping state and achieve exact specification of a site responsible for obstructive sleep apnea syndrome (OSAS).

BRIEF DESCRIPTION OF DRAWINGS

FIG. 10 illustrates the relationship between the difference in nasal cavity resistance and an amount of increment or decrement of a pixel density value;

DESCRIPTION OF EMBODIMENTS

Embodiments of the disclosure will now be described in detail with reference to the accompanying drawings.

Embodiment 1

Embodiment 1 of the disclosure will now be described.

Figure 1:
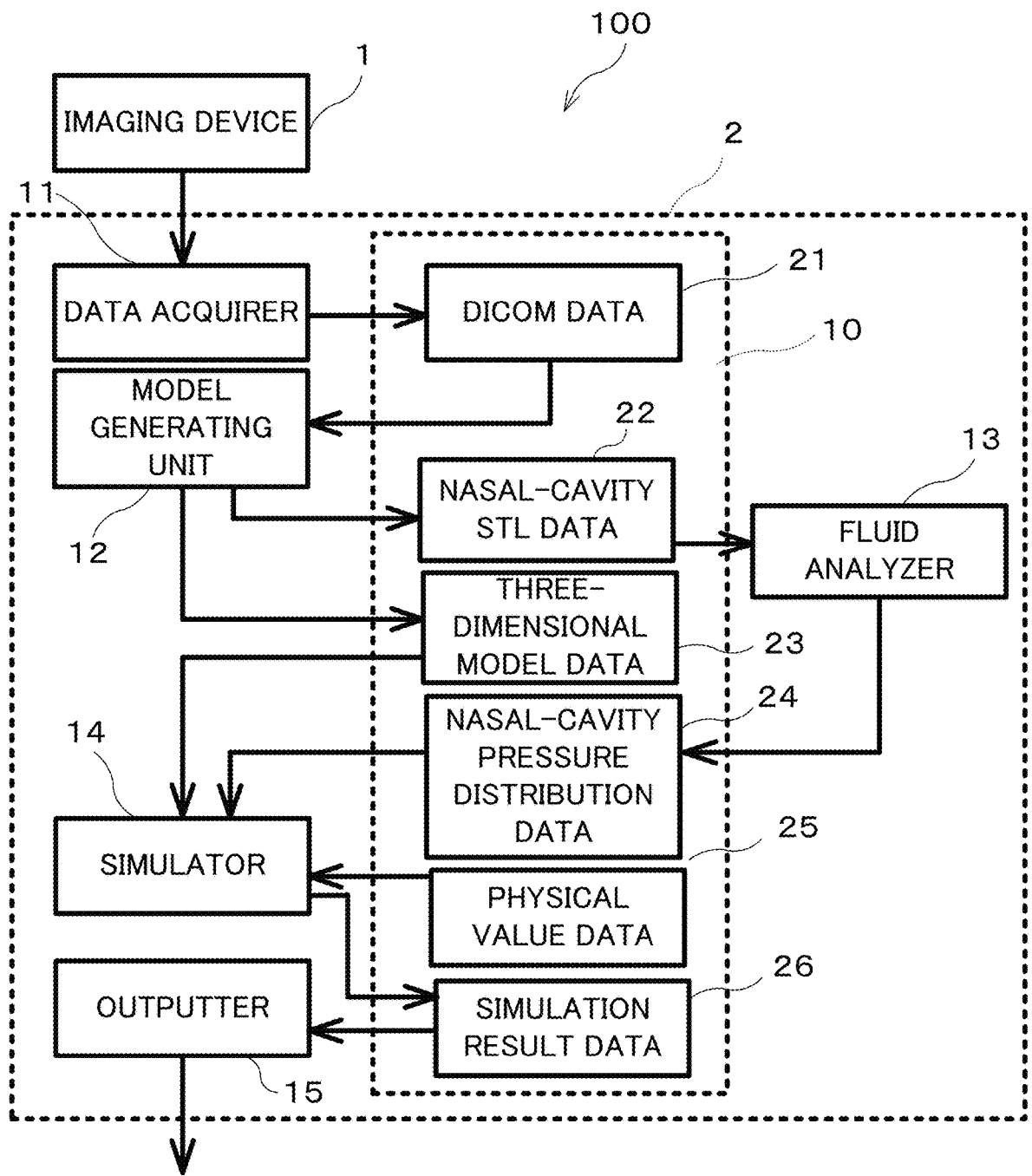
FIG. 1 is a block diagram illustrating a schematic configuration of a diagnostic system according to Embodiment 1 of the disclosure.

A diagnostic system 100 according to Embodiment 1 illustrated in FIG. 1 is used to simulate the ventilation condition of the upper airway of a human body (subject) on a computer and thus specify a site responsible for sleep apnea syndrome. In order to simulate the ventilation condition of the upper airway of the subject, the diagnostic system 100 generates three-dimensional models of the upper airway and its surrounding tissues in the maxillofacial area and a fluid model of the air inside the upper airway, on the basis of three-dimensional image data on the interior of the maxillofacial area of the subject captured by a device, such as an X-ray computer tomography (CT) device. The upper airway is defined as encompassing the nose, nasal cavities, nasopharynx, pharynx, and larynx.

The diagnostic system 100 also executes simulation based on fluid-structure coupled analysis using the three-dimensional models of the upper airway and its surrounding tissues and the fluid model of the air inside the upper airway. The diagnostic system 100 provides the three-dimensional models of the upper airway and its surrounding tissues and the fluid model of the air inside the upper airway with the individual peculiar physical values and executes the simulation based on the fluid-structure coupled analysis. This simulation can reveal the interaction between deformation of the upper airway and its surrounding tissues that varies depending on respiration and the air flow inside the upper airway caused by respiration, thereby exactly simulating both the air flow (pressure distribution and flow velocity distribution) inside the upper airway and the deformation of the upper airway due to the deformation of the surrounding tissues during respiration. The simulation can thus achieve more exact specification of the site responsible for sleep apnea syndrome.

With reference to FIG. 1, the diagnostic system 100 includes an imaging device 1 and a computer 2. The imaging device 1 is connected to the computer 2 via a communication network. The communication network enables the imaging device 1 and the computer 2 to transmit and receive data to and from each other.

The imaging device 1 is an X-ray CT device. The imaging device 1 captures a three-dimensional X-ray CT image of the maxillofacial area of the subject. The imaging device 1 is equipped with an X-ray tube and a detector. During an X-ray CT scanning process, the X-rays are emitted from the X-ray tube, pass through the subject, and are then detected by the detector. The result of detection by the detector is stored into the imaging device 1 in the form of raw data.

The imaging device 1 conducts image reconstruction based on the stored raw data and thus generates cross-sectional image data (slice image data) on the maxillofacial area of the subject. Based on the slice image data, the imaging device 1 generates three-dimensional image data on the interior of the maxillofacial area of the subject. The three-dimensional image data is composed of pixels each having a pixel density value (CT value (Hu)) indicating the state of material at each position in the three-dimensional space.

The above-explained process can yield the three-dimensional image data on the interior of the maxillofacial area of the subject. The resulting three-dimensional image data is transmitted to the computer 2 in the form of digital imaging and communications in medicine (DICOM) data via the communication network.

The DICOM data is defined as data generated in accordance with the DICOM format. The DICOM format is mainly used for medical image data. The DICOM data contains the above-mentioned three-dimensional image data and auxiliary information in accordance with the DICOM format. The auxiliary information indicates attribute information on the image data, such as patient information, imaging condition information, image information, and display information, and is embedded in the DICOM data in the form of tag information.

On the basis of the three-dimensional X-ray CT image data contained in the received DICOM data, the computer 2 generates three-dimensional models of the upper airway and its surrounding tissues in the maxillofacial area of the subject. These models are generated by the finite element method involving division of an object into a finite number of elements defined by nodes. That is, the generated models of the upper airway and its surrounding tissues are so-called mesh models composed of multiple elements bonded to each other at the nodes in the mesh shape. The division of the object into elements can be based on the voxel data configuring medical image data.

The computer 2 then provides the three-dimensional mesh models of the upper airway and its surrounding tissues in the maxillofacial area with the individual peculiar physical values and executes simulation based on the fluid-structure coupled analysis according to respiration of the subject, to thereby acquire information on the ventilation condition of the upper airway.

Figure 2:
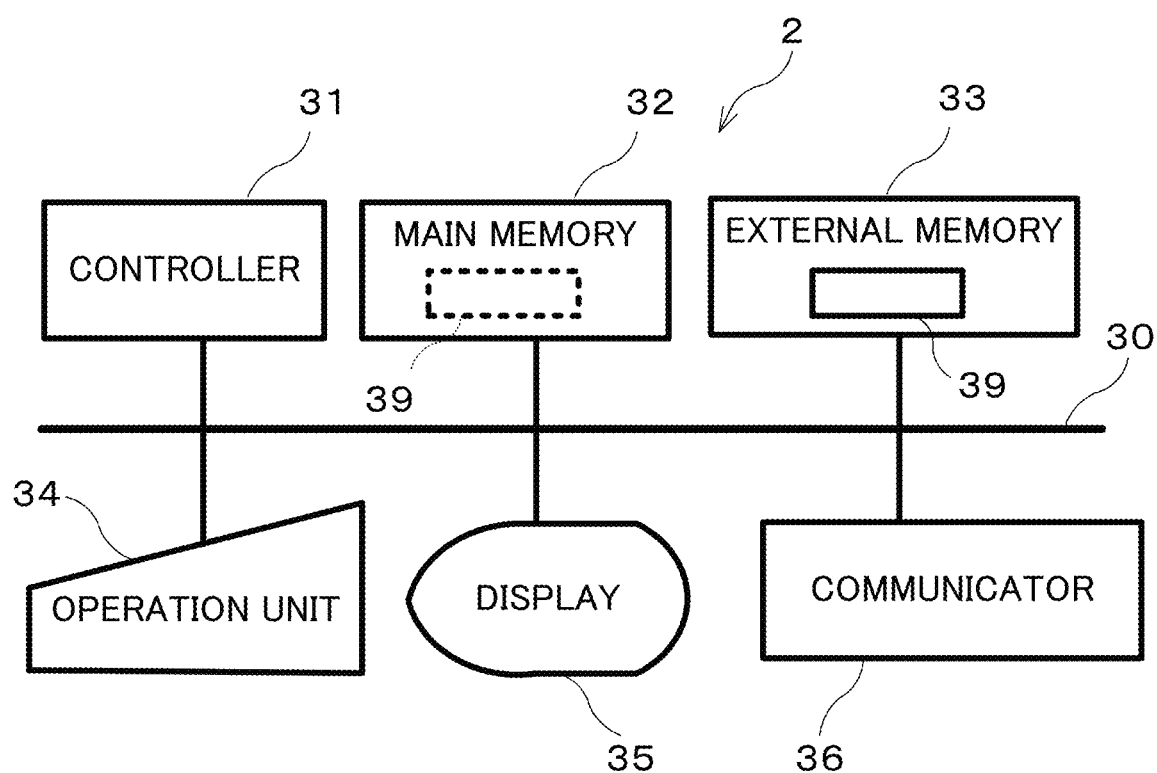
FIG. 2 is a block diagram illustrating a hardware configuration of a computer.

With reference to FIG. 2, which illustrates a hardware configuration of the computer 2 in FIG. 1, the computer 2 is equipped with a controller 31, a main memory 32, an external memory 33, an operation unit 34, a display 35, and a communicator 36. Each of the main memory 32, the external memory 33, the operation unit 34, the display 35, and the communicator 36 is connected to the controller 31 via an internal bus 30.

The controller 31 includes a central processing unit (CPU). The CPU executes a program 39 stored in the external memory 33 and thus achieves the functions of the components of the computer 2 illustrated in FIG. 1.

The main memory 32 includes a random-access memory (RAM). The program 39 stored in the external memory 33 is loaded into the main memory 32. In addition, the main memory 32 serves as a work area (area for temporarily storing data) of the controller 31.

The external memory 33 includes a non-volatile memory, such as a flash memory, a hard disk, a digital versatile disc random-access memory (DVD-RAM), or a digital versatile disc rewritable (DVD-RW). The external memory 33 preliminarily stores the program 39 to be executed by the controller 31. The external memory 33 also supplies the controller 31 with data to be used in execution of the program 39 and stores data supplied from the controller 31 in accordance with the instructions from the controller 31.

The operation unit 34 includes a keyboard, a pointing device (for example, a mouse), and an interface device that connects the keyboard and the pointing device to the internal bus 30. The operation unit 34 receives information on manipulation of an operator and inputs the information to the controller 31.

The display 35 includes a cathode ray tube (CRT), a liquid crystal display (LCD), or an organic electroluminescence (EL). The display 35 displays an operation screen if the operator inputs operation information. The display 35 displays the shape of the upper airway of the subject and information on the ventilation condition, as described below.

The communicator 36 includes a serial or parallel interface. The communicator 36 is connected to the imaging device 1 via the communication network and thus receives the three-dimensional X-ray CT image data transmitted from the imaging device 1.

The functions of the individual components of the computer 2 illustrated in FIG. 1 are achieved by execution of the program 39 illustrated in FIG. 2 using hardware resources, such as the controller 31, the main memory 32, the external memory 33, the operation unit 34, the display 35, and the communicator 36.

The computer 2 having the hardware configuration illustrated in FIG. 2 has a functional configuration including a storage 10, a data acquirer 11, a model generating unit 12, a fluid analyzer 13, a simulator 14, and an outputter 15, as illustrated in FIG. 1.

The storage 10 corresponds to the external memory 33 illustrated in FIG. 2 of the hardware configuration illustrated in FIG. 2. The storage 10 stores various types of data. Examples of the data stored in the storage 10 include DICOM data 21.

The data acquirer 11 corresponds to the controller 31 and the communicator 36 of the hardware configuration illustrated in FIG. 2. The data acquirer 11 receives three-dimensional X-ray CT image data (DICOM data) on the maxillofacial area transmitted from the imaging device 1. The data acquirer 11 stores the received DICOM data 21 into the storage 10.

The model generating unit 12 corresponds to the controller 31 of the hardware configuration illustrated in FIG. 2. The model generating unit 12 receives input of the DICOM data 21 stored in the storage 10, that is, the three-dimensional image data on the interior of the maxillofacial area of the subject. The model generating unit 12 uses the DICOM data 21 and thus generates three-dimensional models of the upper airway and its surrounding tissues and a fluid model of the air inside the upper airway by the finite element method.

The three-dimensional models of the upper airway and its surrounding tissues are built based on governing equations that represent the structures and deformation of the shapes of the individual tissues. Examples of the tissues surrounding the upper airway include bones, a tongue, a soft palate, and soft tissues, such as maxillofacial muscles.

The fluid model is constructed based on governing equations (for example, the Bernoulli equation and the Navier-Stokes equations) of fluid that have information on the air flow, such as the pressure and flow velocity of the fluid, as variables.

Figure 3:
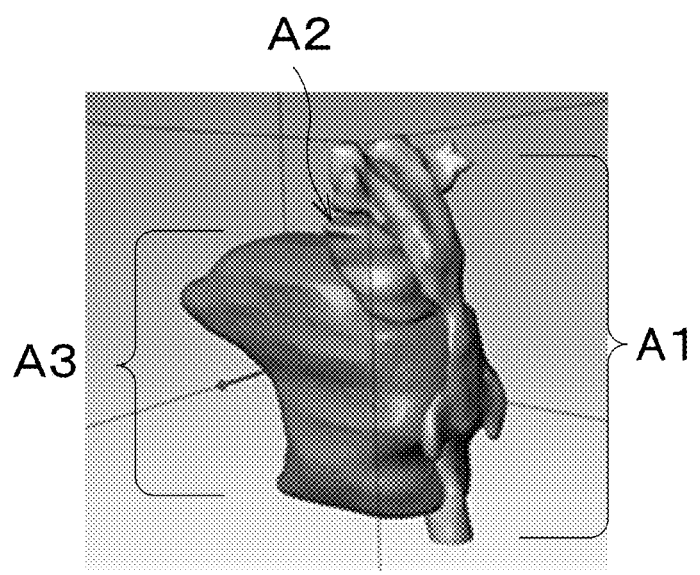
FIG. 3 illustrates an exemplary three-dimensional image of an upper airway, a tongue, and a soft palate.

FIG. 3 illustrates an exemplary three-dimensional image of an upper airway, a tongue, and a soft palate. A1 represents the upper airway, A2 represents the soft palate, and A3 represents the tongue. As illustrated in FIG. 3, the tongue A3 and the soft palate A2 are tissues surrounding the upper airway and located adjacent to the upper airway A1. The tongue A3 is known as a typical site responsible for sleep apnea syndrome because the tongue A3 hangs down and presses the upper airway when the subject lies in a supine position.

Figure 4:
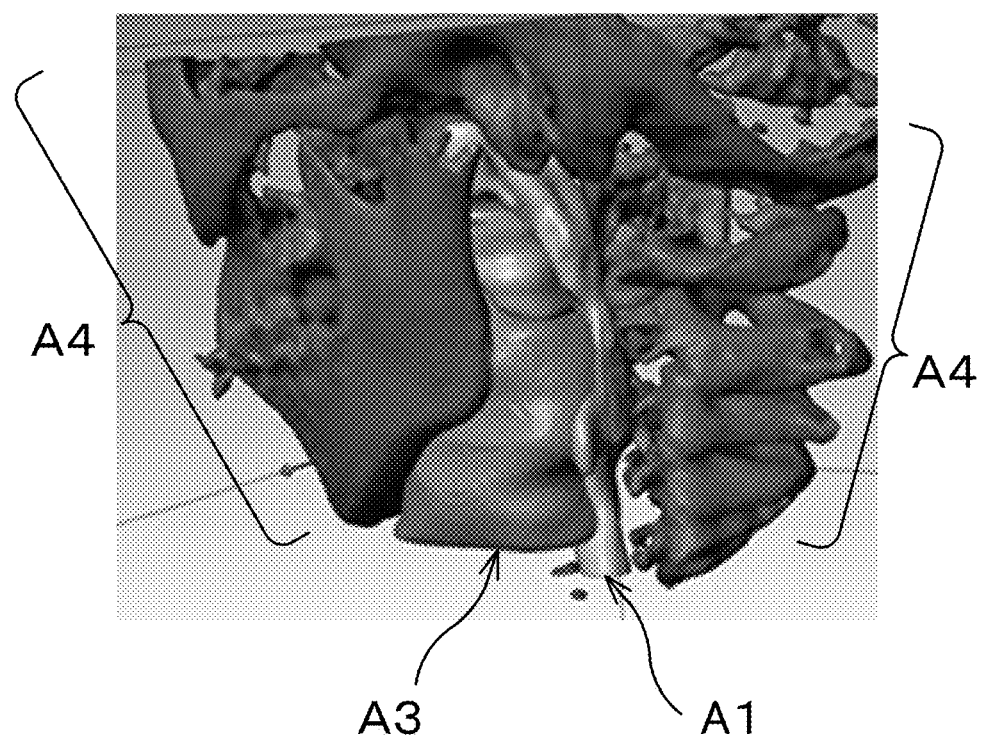
FIG. 4 illustrates an exemplary three-dimensional image of an upper airway, a tongue, a soft palate, and bones.

FIG. 4 illustrates a three-dimensional image of bones, in addition to the upper airway, the soft palate, and the tongue. A4 represents the bones. As illustrated in FIG. 4, the upper airway, the tongue, and the soft palate are surrounded by a mandibular bone and a cervical spine. These mandibular bone and cervical spine are also regarded as tissues surrounding the upper airway and included in the generated three-dimensional models.

Figure 5:
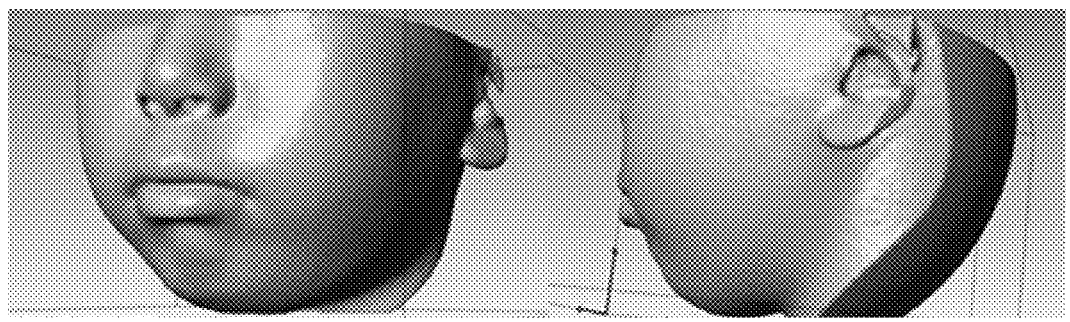
FIG. 5 illustrates an exemplary three-dimensional image of soft tissues including muscles around a jaw.

FIG. 5 illustrates an exemplary three-dimensional image of soft tissues including muscles and fat around the jaw. These soft tissues around the jaw are also regarded as tissues surrounding the upper airway and included in the generated three-dimensional models, because enlargement of the soft tissues around the jaw significantly affects respiration.

Figure 6:
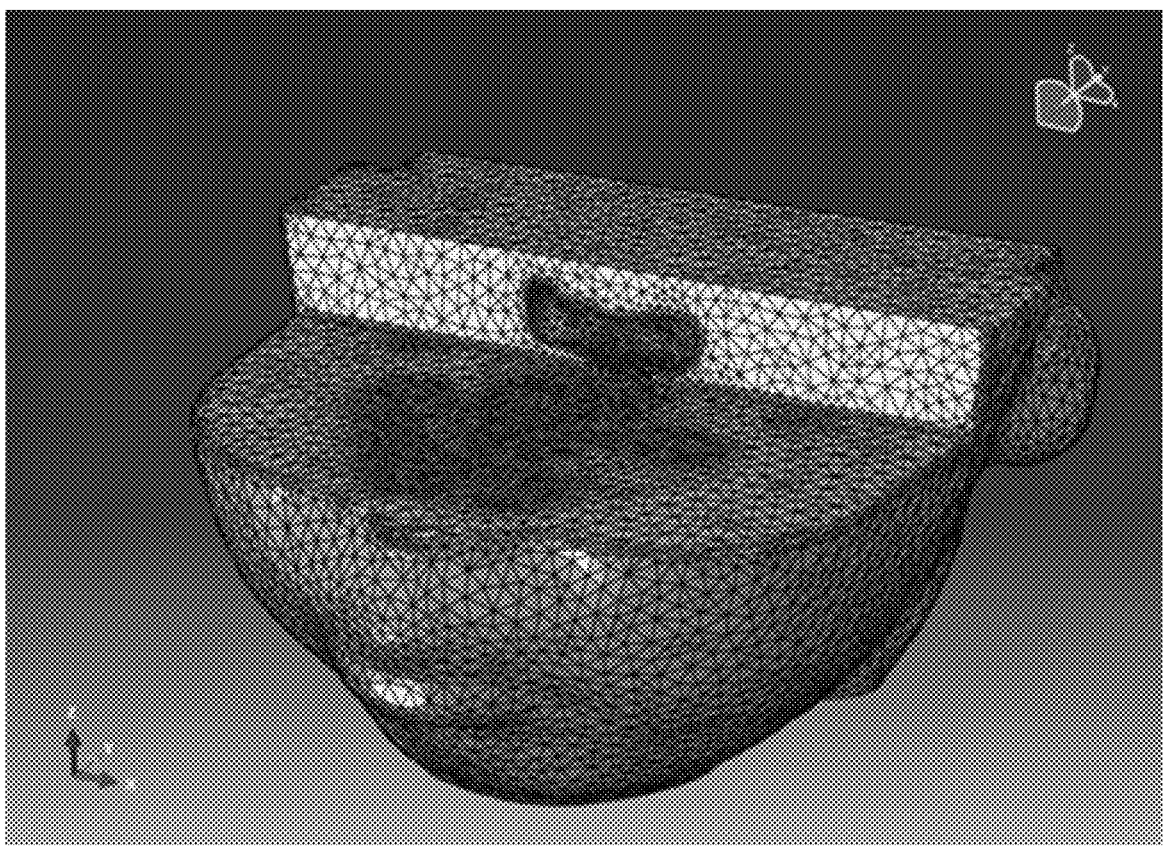
FIG. 6 illustrates an exemplary three-dimensional mesh model of an upper airway and its surrounding tissues.

FIG. 6 illustrates an exemplary three-dimensional mesh model of the upper airway, the tongue, the soft palate, the bones, and the soft tissues around the jaw. In this three-dimensional model, the boundary between different tissues has common nodes connecting the elements to each other, so that the upper airway and its surrounding tissues can be deemed as a single three-dimensional model. This three-dimensional model can therefore simulate the situation in which deformation of each tissue causes deformation of its surrounding tissues.

The model generating unit 12 separately generates a three-dimensional model of the nasal cavities and a three-dimensional model of the pharynx and the portions therebelow of the upper airway. The model of the nasal cavities is generated in the form of standard triangulated language (STL) data. The STL data indicates the three points of triangular patches used to approximate a three-dimensional object. In the STL data, the object has a polygonal surface defined by triangular patches (facets).

Figure 7:
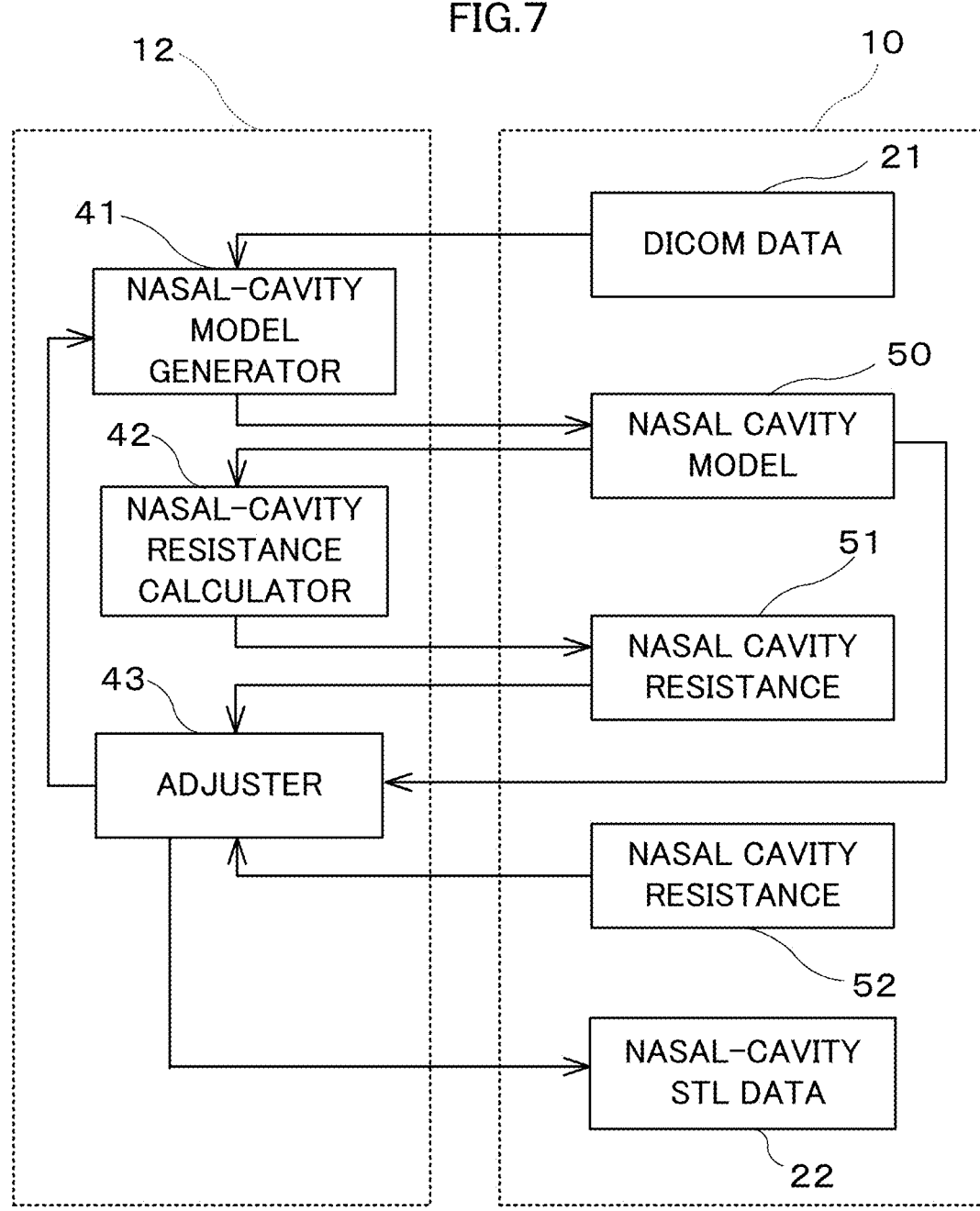
FIG. 7 is a block diagram illustrating a configuration for generating a nasal cavity model.

A procedure of generating STL data on the nasal cavities, that is, a three-dimensional model of the nasal cavities (nasal cavity model) will now be explained in detail. FIG. 7 illustrates a configuration for generating the nasal cavity model that mainly includes the model generating unit 12. As illustrated in FIG. 7, the model generating unit 12 includes a nasal-cavity model generator 41, a nasal-cavity resistance calculator 42, and an adjuster 43.

Figure 8:
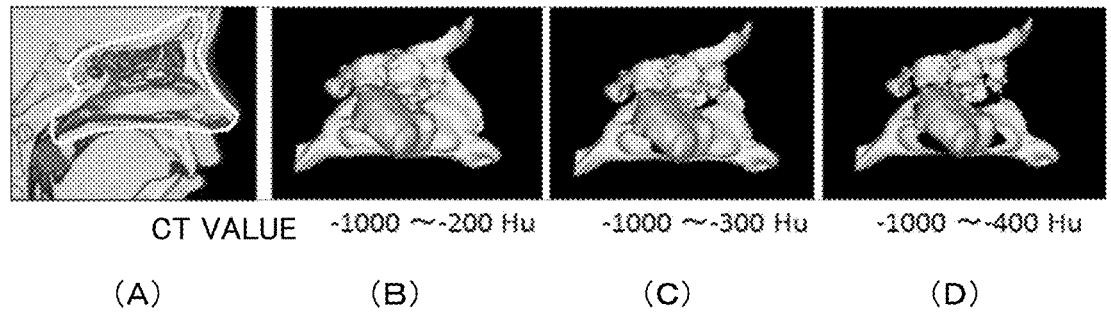
FIG. 8 illustrates a nasal cavity model that varies depending on the defined range of CT value.

The nasal-cavity model generator 41 extracts pixels having pixel density values within a specific range from the three-dimensional image data on the nasal cavities of the subject contained in the DICOM data 21. The nasal-cavity model generator 41 then generates a nasal cavity model 50, which is a three-dimensional model of the nasal cavities, based on the three-dimensional image data composed of the extracted pixels. The generated nasal cavity model 50 is stored into the storage 10. As illustrated with the white contour in the section (A) of FIG. 8, the three-dimensional image data on the area ranging from the nose to the pharynx is extracted as the three-dimensional image data on the nasal cavities of the subject. Specifically, the nasal-cavity model generator 41 extracts pixels having CT values within the specific range (for example, within the range of −1000 to −200 Hu) from the three-dimensional image data on the nasal cavities, and generates a nasal cavity model based on the three-dimensional image data composed of the extracted pixels (refer to the section (B) of FIG. 8). The nasal-cavity model generator 41 may also extract pixels having CT values within the specific range (for example, within the range of −1000 to −300 Hu or the range of −1000 to −400 Hu) and generate a nasal cavity model based on the three-dimensional image data composed of the extracted pixels (refer to the sections (C) and (D) of FIG. 8).

Figure 9:
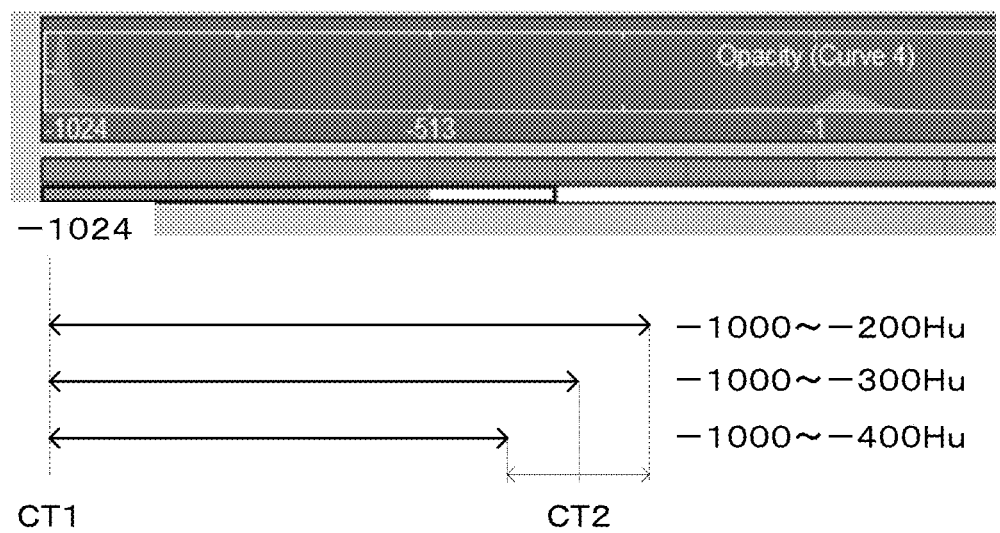
FIG. 9 illustrates the relationship between the range of CT value and materials.

With reference to FIG. 9, the air has a CT value of approximately −1000 Hu and the water has a CT value of 0 Hu. The soft tissues of the subject have CT values between −1000 and 0 Hu. In general, the resulting nasal cavity model has a different shape depending on the defined range of CT value, as illustrated in the sections (B) to (D) of FIG. 8, because the CT values are affected by imaging conditions (for example, soft tissues of the subject, metals, imaging apparatuses).

Since the resulting nasal cavity model has a different shape depending on the defined range of CT value, the range of CT value is calibrated in this embodiment so as to obtain a nasal cavity model that is most approximate to the actual shape of the nasal cavities of the subject. This calibration uses a nasal cavity resistance, which is clinically-used index data for evaluation of the ventilation condition of the nasal cavities. The nasal cavity resistance is measured with a nasal-cavity draft gauge. The nasal cavity resistance is expressed with a unit of Pa/ml/s and a normal nasal cavity resistance is about 0.5 Pa/ml/s.

The nasal-cavity resistance calculator 42 calculates a nasal cavity resistance 51 through fluid analysis using the nasal cavity model 50 generated by the nasal-cavity model generator 41. The calculated nasal cavity resistance 51 is stored into the storage 10. The storage 10 also stores a nasal cavity resistance 52, which is a value actually measured with the nasal-cavity draft gauge.

The adjuster 43 adjusts the range of pixel density value of the pixels to be extracted for generation of the nasal cavity model 50 by the nasal-cavity model generator 41, such that the nasal cavity resistance 51 calculated by the nasal-cavity resistance calculator 42 is equal to the nasal cavity resistance 52 actually measured with the nasal-cavity draft gauge. The adjuster 43 stores the nasal cavity model 50, of which the nasal cavity resistance 51 calculated through the fluid analysis equals to the nasal cavity resistance 52 actually measured with the nasal-cavity draft gauge, into the storage 10 in the form of the nasal-cavity STL data 22.

More specifically, the nasal-cavity model generator 41 generates the nasal cavity model 50 using the pixels having pixel density values within the range defined by a first pixel density value CT1 (for example, −1000 Hu) approximate to the pixel density value of the air and a second pixel density value CT2 (for example, a CT value within the range of −400 to −200 Hu) larger than the first pixel density value CT1. The adjuster 43 adjusts the second pixel density value CT2 such that the nasal cavity resistance 51 calculated by the nasal-cavity resistance calculator 42 is equal to the nasal cavity resistance 52 actually measured with the nasal-cavity draft gauge.

The adjuster 43 increments the second pixel density value CT2 if the nasal cavity resistance 51 calculated by the nasal-cavity resistance calculator 42 is larger than the nasal cavity resistance 52 actually measured with the nasal-cavity draft gauge. The adjuster 43 decrements the second pixel density value CT2 if the nasal cavity resistance 51 calculated by the nasal-cavity resistance calculator 42 is smaller than the nasal cavity resistance 52 actually measured with the nasal-cavity draft gauge. As the nasal cavity resistance 51 calculated by the nasal-cavity resistance calculator 42 approaches the nasal cavity resistance 52 actually measured with the nasal-cavity draft gauge, the adjuster 43 decreases the amount of increment or decrement of the second pixel density value CT2. The nasal cavity resistance 51 is represented by "R1" and the nasal cavity resistance 52 is represented by "R2" in the following description. The above-explained process of adjusting the range of CT value by the adjuster 43 enables the range of CT value to approach the optimal range without excessive overshoot or delay.

For example, as illustrated in FIG. 10, if the difference R1−R2 between the nasal cavity resistance R1 calculated through the fluid analysis and the nasal cavity resistance R2 measured with the nasal-cavity draft gauge is equal to or larger than +0.5 Pa/ml/s (the unit is omitted in the following description), the nasal-cavity model generator 41 regenerates the nasal cavity model 50 using the second pixel density value CT2 incremented by +100 Hu. If the difference R1−R2 is equal to or larger than +0.3 and smaller than +0.5, the nasal-cavity model generator 41 regenerates the nasal cavity model 50 using the second pixel density value CT2 incremented by +50 Hu. If the difference R1−R2 is equal to or larger than +0.1 and smaller than +0.3, the nasal-cavity model generator 41 regenerates the nasal cavity model 50 using the second pixel density value CT2 incremented by +20 Hu. If the difference R1−R2 is equal to or larger than +0.05 and smaller than +0.1, the nasal-cavity model generator 41 regenerates the nasal cavity model 50 using the second pixel density value CT2 incremented by +10 Hu. If the difference R1−R2 is larger than −0.05 and smaller than +0.05, the adjuster 43 determines the two resistances to be equal to each other and stores the outstanding nasal cavity model 50 into the storage 10 in the form of the nasal-cavity STL data 22.

In addition, if the difference R1−R2 is equal to or smaller than −0.05 and larger than −0.1, the nasal-cavity model generator 41 regenerates the nasal cavity model 50 using the second pixel density value CT2 decremented by −10 Hu. If the difference R1−R2 is equal to or smaller than −0.1 and larger than −0.3, the nasal-cavity model generator 41 regenerates the nasal cavity model 50 using the second pixel density value CT2 decremented by −20 Hu. If the difference R1−R2 is equal to or smaller than −0.3 and larger than −0.5, the nasal-cavity model generator 41 regenerates the nasal cavity model 50 using the second pixel density value CT2 decremented by −50 Hu. If the difference R1−R2 is equal to or smaller than −0.5, the nasal-cavity model generator 41 regenerates the nasal cavity model 50 using the second pixel density value CT2 decremented by −100 Hu.

As explained above, the model generating unit 12 repeats generating the nasal cavity model 50 while varying the second pixel density value CT2 depending on the difference R1−R2, and stores the nasal cavity model 50, of which the nasal cavity resistance 51 is equal to the result of measurement with the nasal-cavity draft gauge, into the storage 10 in the form of the nasal-cavity STL data 22.

Figure 11:
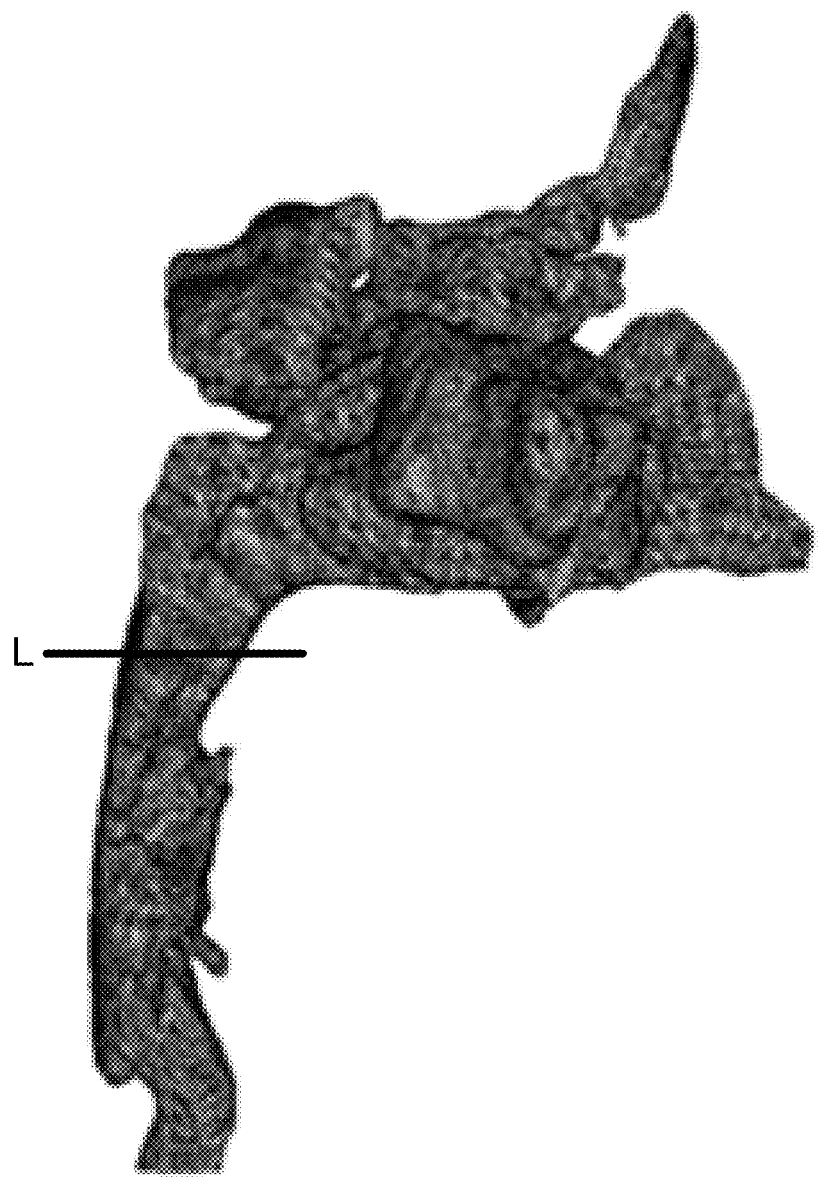
FIG. 11 illustrates an exemplary three-dimensional image of an upper airway.

FIG. 11 illustrates an exemplary three-dimensional image of the upper airway. In FIG. 11, the area above the line L corresponds to the nasal cavity area. In this embodiment, the area above the line L is stored into the storage 10 in the form of the nasal-cavity STL data 22.

The model generating unit 12 also generates a three-dimensional mesh model of the pharynx and the portions therebelow of the upper airway. The resulting three-dimensional mesh model of the pharynx and the portions therebelow and the three-dimensional mesh model of the other tissues are stored into the storage 10 in the form of three-dimensional model data 23.

The fluid analyzer 13 corresponds to the controller 31 of the hardware configuration illustrated in FIG. 2. The fluid analyzer 13 uses the nasal-cavity STL data 22 and calculates information on the ventilation condition of the nasal cavities through the fluid analysis over a respiratory cycle assuming that the nasal cavities are a rigid body. The nasal cavities are assumed to be a rigid body because fluid-structure coupled analysis of the nasal cavities is difficult due to its complicated internal configuration and substantially no change in the shapes of the airways. Examples of the calculated information on the ventilation condition of the nasal cavities include a pressure distribution inside the nasal cavities.

Figure 12:
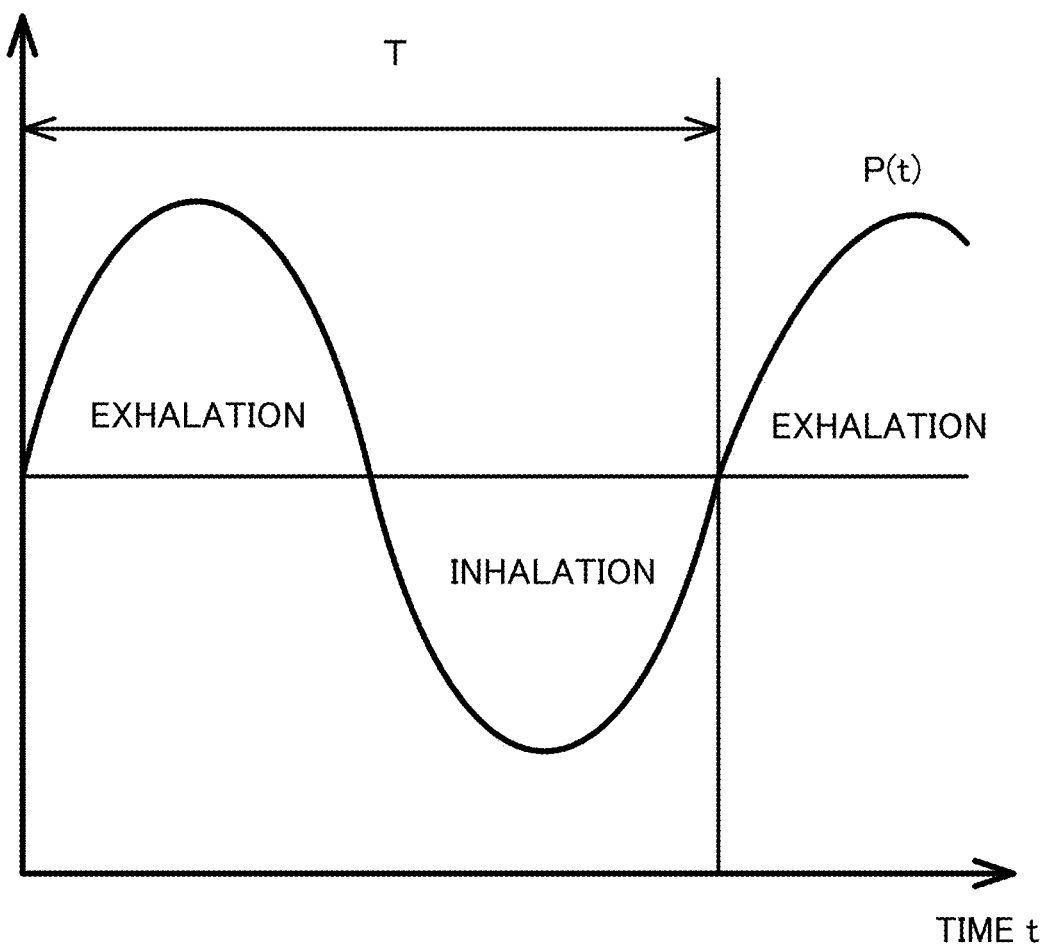
FIG. 12 illustrates an exemplary cross-sectional average pressure at the boundary between nasal cavities and a pharynx over a respiratory cycle.

The fluid analyzer 13 calculates a cross-sectional average pressure P(t) at the boundary between the nasal cavities and the pharynx on the basis of the pressure distribution inside the nasal cavities. FIG. 12 illustrates an exemplary cross-sectional average pressure P(t) at the boundary between the nasal cavities and the pharynx over a respiratory cycle. As illustrated in FIG. 12, the cross-sectional average pressure P(t) varies in a cycle T depending on the repetition of exhalation and inhalation. The air inside the nasal cavities has a positive pressure relative to the atmospheric pressure during exhalation and has a negative pressure relative to the atmospheric pressure during inhalation.

The simulator 14 corresponds to the controller 31 of the hardware configuration illustrated in FIG. 2. The simulator 14 provides the three-dimensional models and the fluid model generated by the model generating unit 12 with peculiar physical values, and executes simulation based on the fluid-structure coupled analysis for the upper airway and its surrounding tissues and the air inside the upper airway according to respiration of the subject, thereby calculating information on the ventilation condition of the upper airway that varies depending on respiration.

The simulation based on the fluid-structure coupled analysis is simulation based on numerical analysis for analyzing a phenomenon that a solid structure is deformed by a force of a fluid flow. The tissues surrounding the upper airway are often found to be a fundamental cause of sleep apnea syndrome. Accordingly, the simulation based on the fluid-structure coupled analysis is executed for an area including the tissues surrounding the upper airway so as to simulate deformation of the tissues surrounding the upper airway in a sleeping state. This procedure can more exactly specify the site responsible for sleep apnea syndrome.

Examples of the peculiar physical values for the three-dimensional models include a Young modulus, coefficient of linear expansion, Poisson ratio, and modulus of transverse elasticity of each tissue. Examples of the peculiar physical values for fluid include a coefficient of viscosity, density, bulk modulus, and Reynolds number of the air. As these physical values, physical value data 25 preliminarily stored in the storage 10 is used. The physical values may be known as physical values of each tissue or values measured for each subject.

The simulator 14 sets the calculated cross-sectional average pressure P(t) at the boundary between the nasal cavities and the pharynx over a respiratory cycle as the initial condition, and executes simulation based on the fluid-structure coupled analysis for the upper airway and its surrounding tissues according to respiration of the subject, using the three-dimensional mesh models of the upper airway and its surrounding tissues excluding the nasal cavities.

The simulator 14 executes simulation based on the fluid-structure coupled analysis for the upper airway and its surrounding tissues according to respiration of the subject, assuming that the three-dimensional models of the surrounding tissues are deformed by the gravity.

Figure 13A:
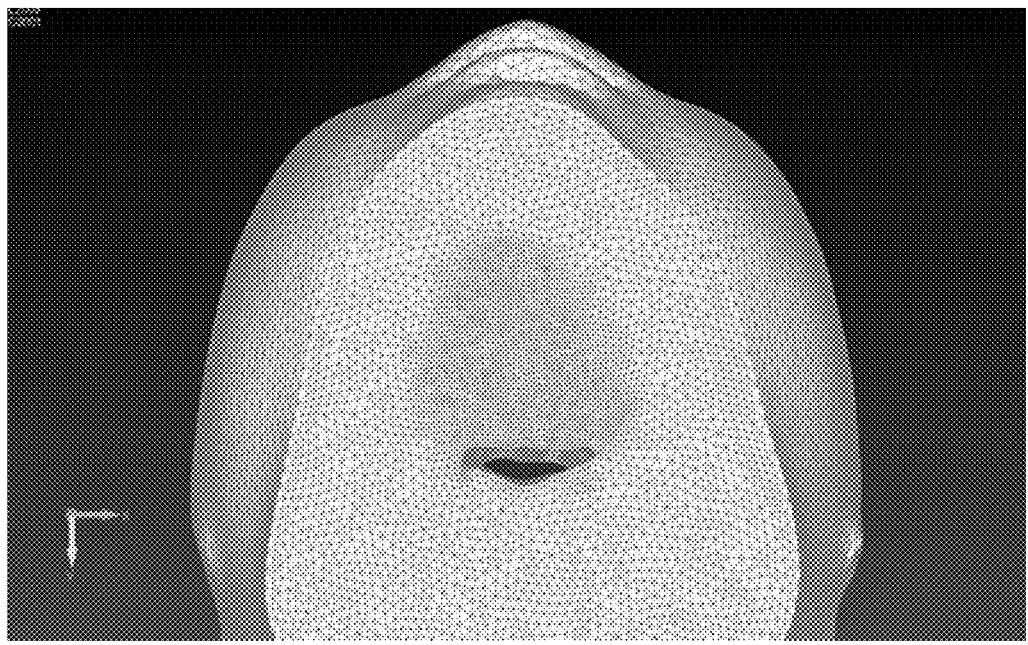
FIG. 13A illustrates an exemplary cross section of an upper airway when a subject does not lie in a supine position.
Figure 13B:
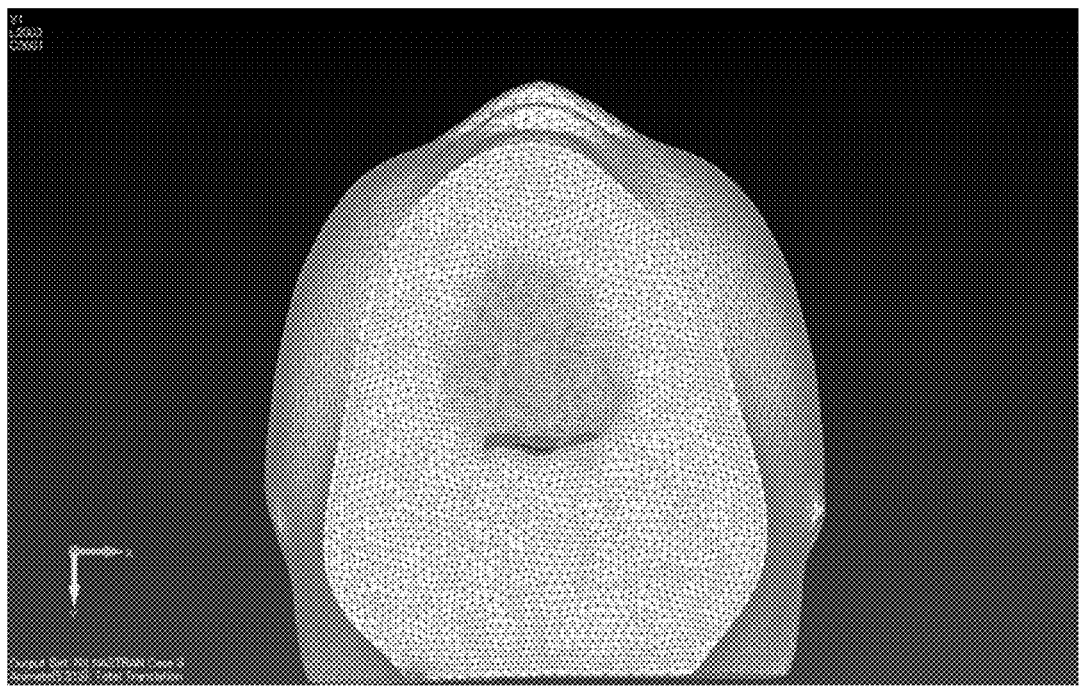
FIG. 13B illustrates an exemplary cross section of the upper airway when the subject lies in a supine position.

FIG. 13A illustrates an exemplary cross section of the upper airway when the subject does not lie in a supine position. FIG. 13B illustrates an exemplary cross section of the upper airway when the subject lies in a supine position. The comparison between FIGS. 13A and 13B reveals that the upper airway is narrower when the subject lies in a supine position. This phenomenon is caused by the tongue hanging down due to the gravity and presses the upper airway.

As explained above, the simulator 14 executes simulation based on the fluid-structure coupled analysis in view of the gravity. The simulator 14 can therefore exactly simulate the upper airway that deforms depending on the posture of the subject and thus calculate the ventilation condition of the upper airway.

The simulator 14 calculates information on the air flow inside the upper airway and deformation of the three-dimensional models of the upper airway and its surrounding tissues. As the information on the air flow inside the upper airway, the simulator 14 calculates a pressure distribution or a flow velocity distribution inside the upper airway or a displacement distribution in the three-dimensional models of the upper airway and its surrounding tissues. This information is stored into the storage 10 in the form of simulation result data 26.

The outputter 15 corresponds to the controller 31 and the display 35 of the hardware configuration illustrated in FIG. 2. The outputter 15 displays a pressure distribution or a flow velocity distribution inside the upper airway or deformation of the upper airway and other tissues.

Figure 14:
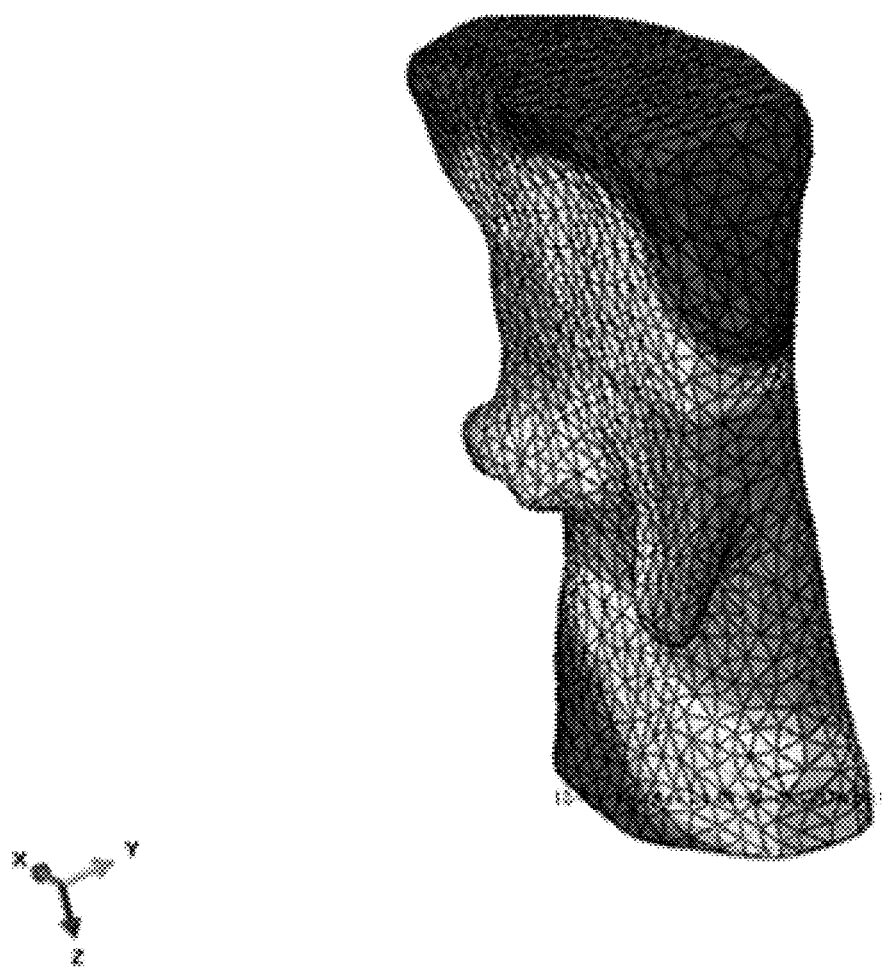
FIG. 14 illustrates an exemplary pressure distribution in the area of a pharynx and an upper airway obtained through fluid-structure coupled analysis according to respiration.
Figure 15:
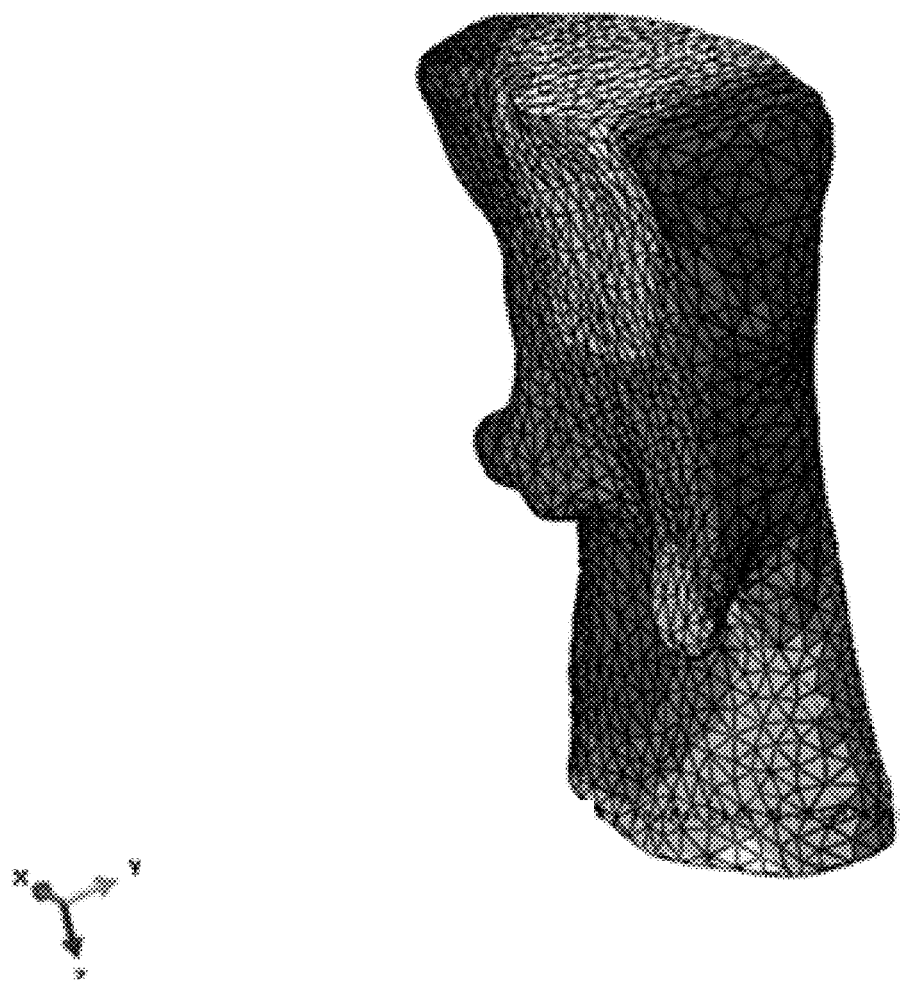
FIG. 15 illustrates an exemplary displacement distribution inside the area of the pharynx and the upper airway obtained through fluid-structure coupled analysis according to respiration.

FIG. 14 illustrates an exemplary pressure distribution inside the area of the pharynx and the upper airway obtained through fluid-structure coupled analysis according to respiration. FIG. 15 illustrates an exemplary displacement distribution inside the area of the pharynx and the upper airway obtained through fluid-structure coupled analysis according to respiration. In FIG. 14, a darker color indicates a higher pressure. In FIG. 15, a darker color indicates a larger displacement. The pressure distribution illustrated in FIG. 14 shows that the upper portion of the upper airway has a higher pressure. The displacement distribution illustrated in FIG. 15 shows that no local portion has a significantly large displacement.

Referring back to FIG. 1, the outputter 15 can also display deformation of the three-dimensional models of the upper airway and its surrounding tissues, through the simulation based on the fluid-structure coupled analysis.

Figure 16:
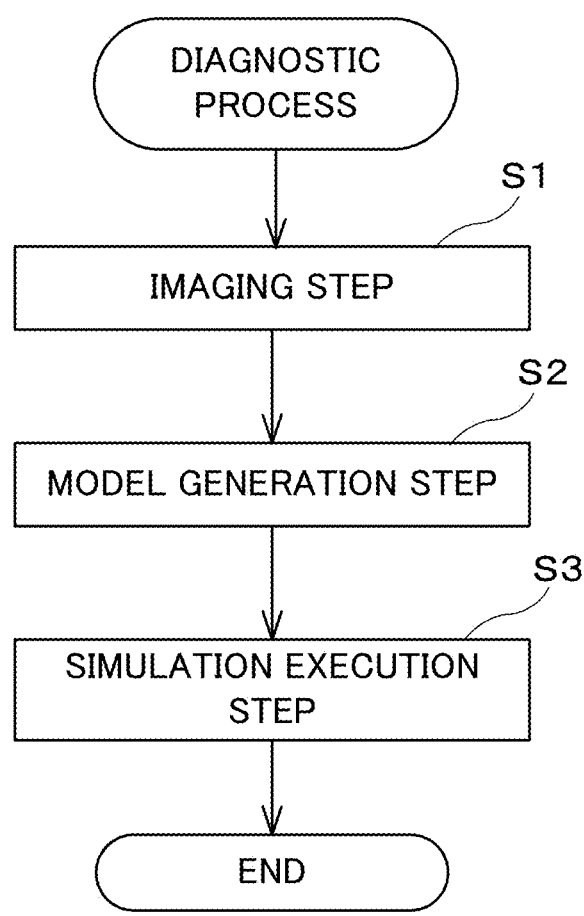
FIG. 16 is a flowchart illustrating a diagnostic process.

The diagnostic process conducted by the diagnostic system 100 will now be explained. With reference to FIG. 16, first, the imaging device 1 executes an imaging step (Step S1). In this imaging step, the imaging device 1 obtains three-dimensional image data on the interior of the maxillofacial area of the subject. This three-dimensional image data is transmitted to the computer 2 and is stored by the data acquirer 11 into the storage 10 of the computer 2 in the form of the DICOM data 21.

Figure 17:
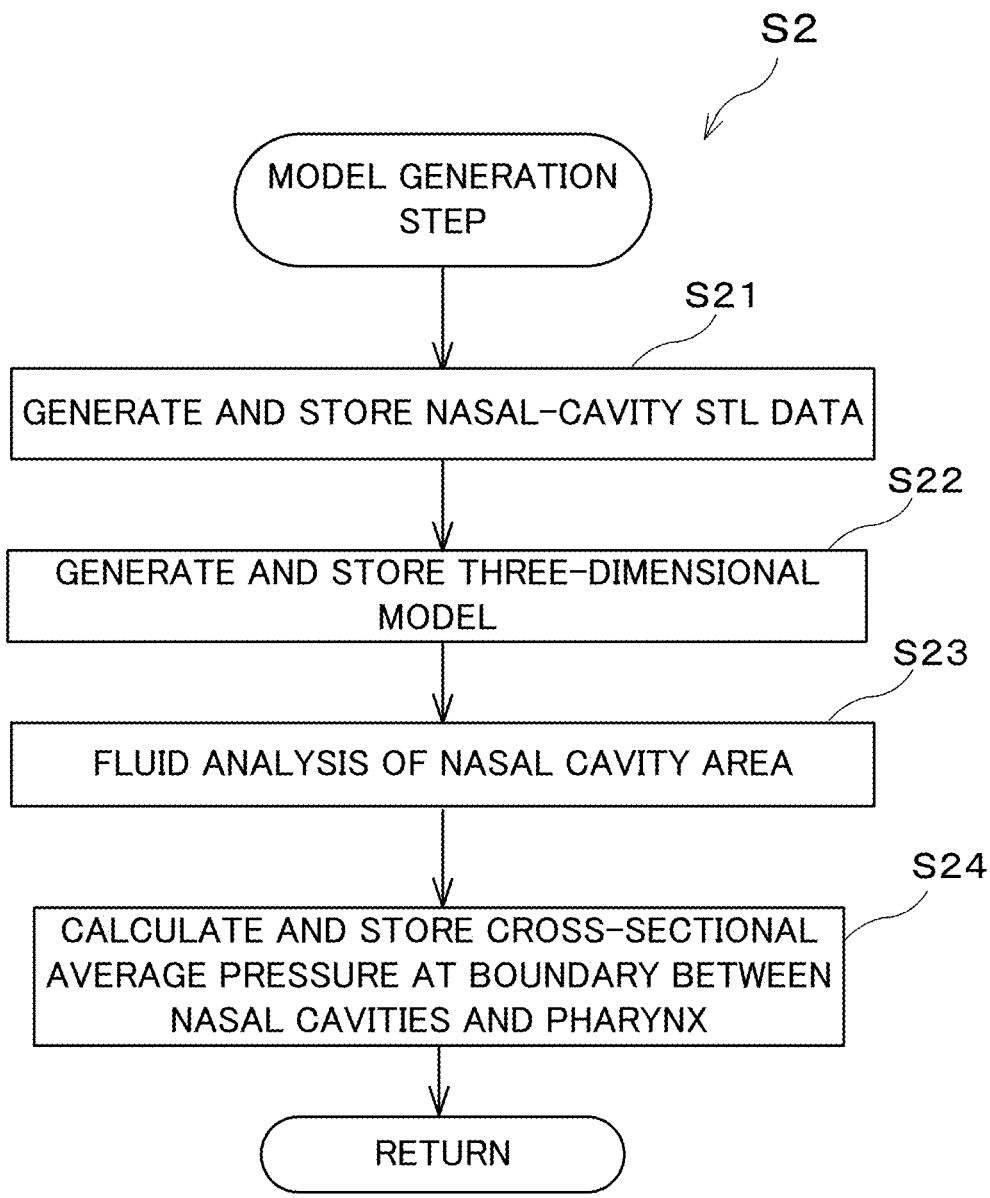
FIG. 17 is a flowchart illustrating a model generation step.

The computer 2 then executes a model generation step (Step S2). In this model generation step, the model generating unit 12 separately generates a three-dimensional model of the nasal cavity area and a three-dimensional model of the area other than the nasal cavity area of the upper airway. With reference to FIG. 17, the model generating unit 12 generates STL data on the nasal cavity area and stores the generated data into the storage 10 in the form of the nasal-cavity STL data 22 (Step S21).

Figure 18:
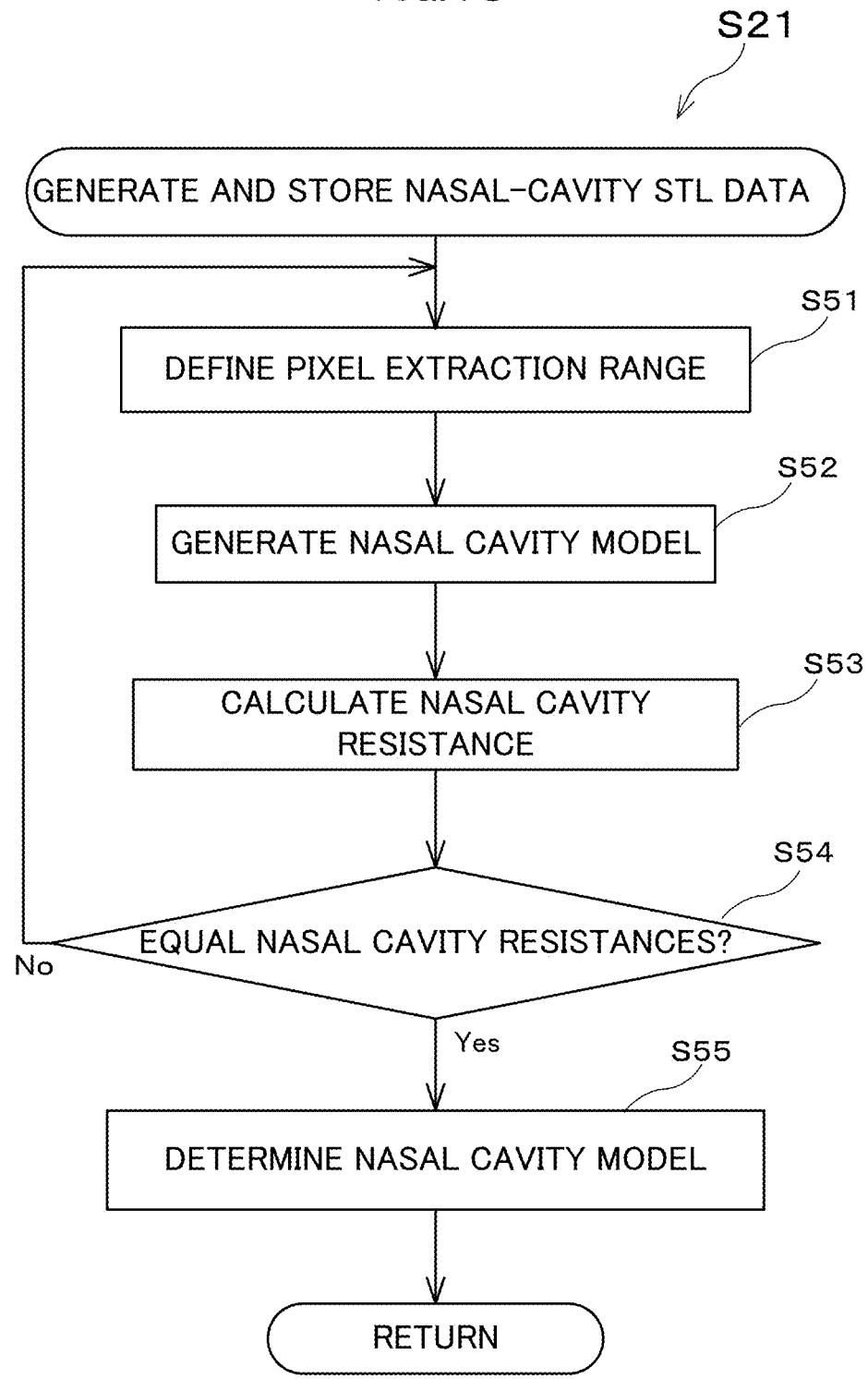
FIG. 18 is a flowchart illustrating a process of generating and storing nasal-cavity STL data.

In Step S21, as illustrated in FIG. 18, the adjuster 43 defines the pixel extraction range (Step S51). In this step, the pixel extraction range (the first pixel density value CT1 and the second pixel density value CT2) is defined to be the initial range.

The nasal-cavity model generator 41 then extracts pixels having pixel density values (CT values) within the defined pixel extraction range and generates the nasal cavity model 50 on the basis of the three-dimensional image data composed of the extracted pixels (Step S52).

Thereafter, the nasal-cavity resistance calculator 42 calculates the nasal cavity resistance 51 through the fluid analysis using the nasal cavity model 50 generated by the nasal-cavity model generator 41 (Step S53). The adjuster 43 determines whether the nasal cavity resistances 51 and 52 are equal to each other (Step S54).

If the nasal cavity resistances 51 and 52 are not equal (Step S54; No), the adjuster 43 redefines the pixel extraction range (Step S51). In this case, an amount of increment or decrement of the second pixel density value CT2 depends on the difference R1–R2 between the nasal cavity resistances R1 and R2 in accordance with the table illustrated in FIG. 10.

If the nasal cavity resistances 51 and 52 are equal (Step S54; Yes), the adjuster 43 determines the outstanding nasal cavity model 50 to be the nasal-cavity STL data 22 and stores this data into the storage 10 (Step S55). In this manner, the adjuster 43 adjusts the range of pixel density value of the pixels to be extracted for generation of the nasal cavity model 50 by the nasal-cavity model generator 41 until the nasal cavity resistance R1 calculated in Step S53 becomes equal to the nasal cavity resistance R2 actually measured with the nasal-cavity draft gauge. The resulting nasal-cavity STL data 22 thus exactly reflects the shapes of the nasal cavities.

Referring back to FIG. 17, the model generating unit 12 generates three-dimensional models of the upper airway and its surrounding tissues and a fluid model of the air inside the upper airway on the basis of the three-dimensional image data (DICOM data 21) on the interior of the maxillofacial area of the subject, and stores these models into the storage 10 in the form of the three-dimensional model data 23 (Step S22). In Step S22, it is preferable that the model generating unit 12, which serves as an upper-airway model generator, extract the pixels having pixel density values within the specific range adjusted by the adjuster 43 from the three-dimensional image data on the interior of the maxillofacial area of the subject and generate three-dimensional models of the tissues of the upper airway on the basis of the three-dimensional image data composed of the extracted pixels. This process can yield the exact three-dimensional models that match the actual upper airway.

The fluid analyzer 13 then calculates a pressure distribution inside the nasal cavities through the fluid analysis of the nasal cavity area on the basis of the nasal-cavity STL data 22, and stores the calculated pressure distribution into the storage 10 in the form of nasal-cavity pressure distribution data 24 (Step S23). The fluid analysis is executed assuming that the nasal cavity area is a rigid body and does not deform. The fluid analyzer 13 calculates the cross-sectional average pressure P(t) at the boundary between the nasal cavities and the pharynx on the basis of the pressure distribution calculated through the fluid analysis, and incorporates the calculated pressure into the nasal-cavity pressure distribution data 24 and stores the combined data into the storage 10 (Step S24).

Figure 19:
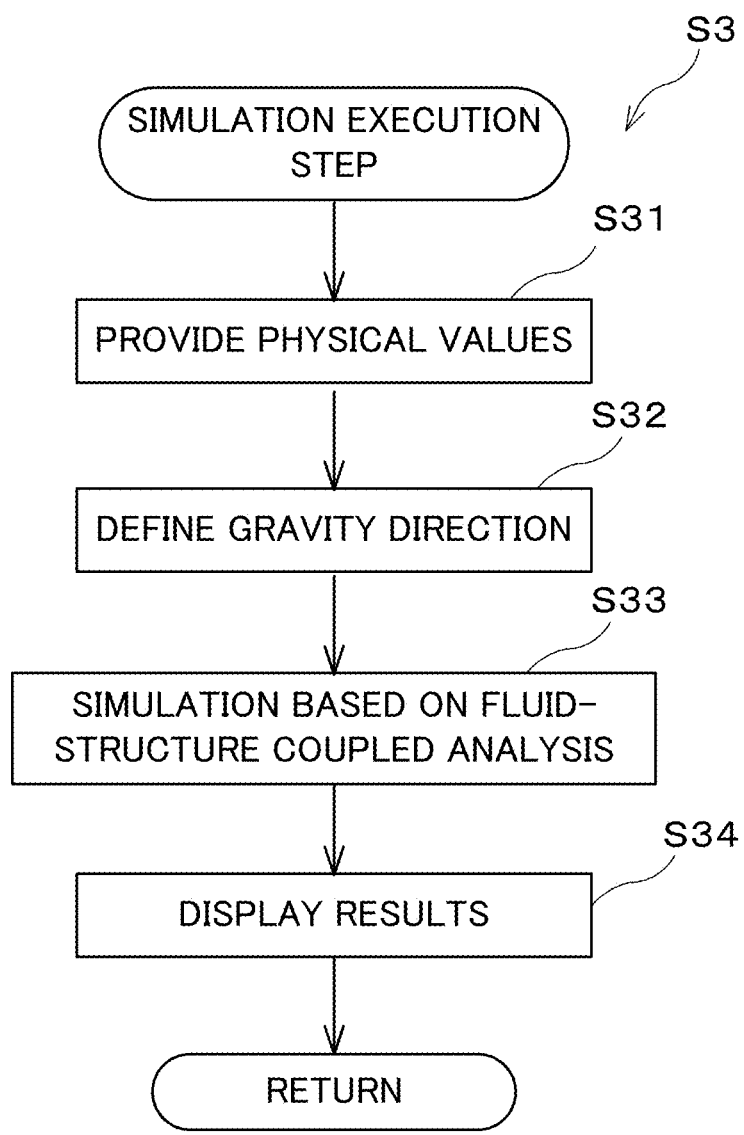
FIG. 19 is a flowchart illustrating a simulation execution step.

Referring back to FIG. 16, the computer 2 conducts a simulation execution step (Step S3). In this simulation execution step, as illustrated in FIG. 19, the simulator 14 provides the individual three-dimensional models of the upper airway and its surrounding tissues with the peculiar physical values with reference to the physical value data 25 stored in the storage 10 (Step S31).

For example, the three-dimensional model of the pharynx and the portions therebelow of the upper airway is provided with the physical values, such as Young moduli or Poisson ratios, peculiar to the individual tissues. For example, the physical value of the tongue is provided to the three-dimensional model of the tongue, the physical value of the soft palate is provided to the three-dimensional model of the soft palate, the physical value of the bones is provided to the three-dimensional models of the bones, and the physical value of the soft tissues is provided to the three-dimensional models of the soft tissues around the jaw.

Thereafter, the simulator 14 defines the gravity direction (Step S32). The gravity direction is defined according to an operation input through the operation unit 34. For example, in the case of diagnosis of the ventilation condition of the upper airway in a supine position, the occipital side of the subject is defined as the bottom.

The simulator 14 then executes simulation based on the fluid-structure coupled analysis (Step S33). The simulation is executed while the three-dimensional models of the upper airway and its surrounding tissues are integrated with the fluid model of the air inside the upper airway.

This simulation uses the cross-sectional average pressure P(t) at the boundary between the nasal cavities and the pharynx of the upper airway as the initial condition. The fluid analysis for analyzing the air flow inside the upper airway and the structural analysis for analyzing deformation of the upper airway and its surrounding tissues are simultaneously executed in view of interaction between the three-dimensional models and the fluid model, to thereby calculate a pressure distribution and a flow velocity distribution inside the upper airway and a displacement distribution inside the upper airway over a respiratory cycle.

Figure 20:
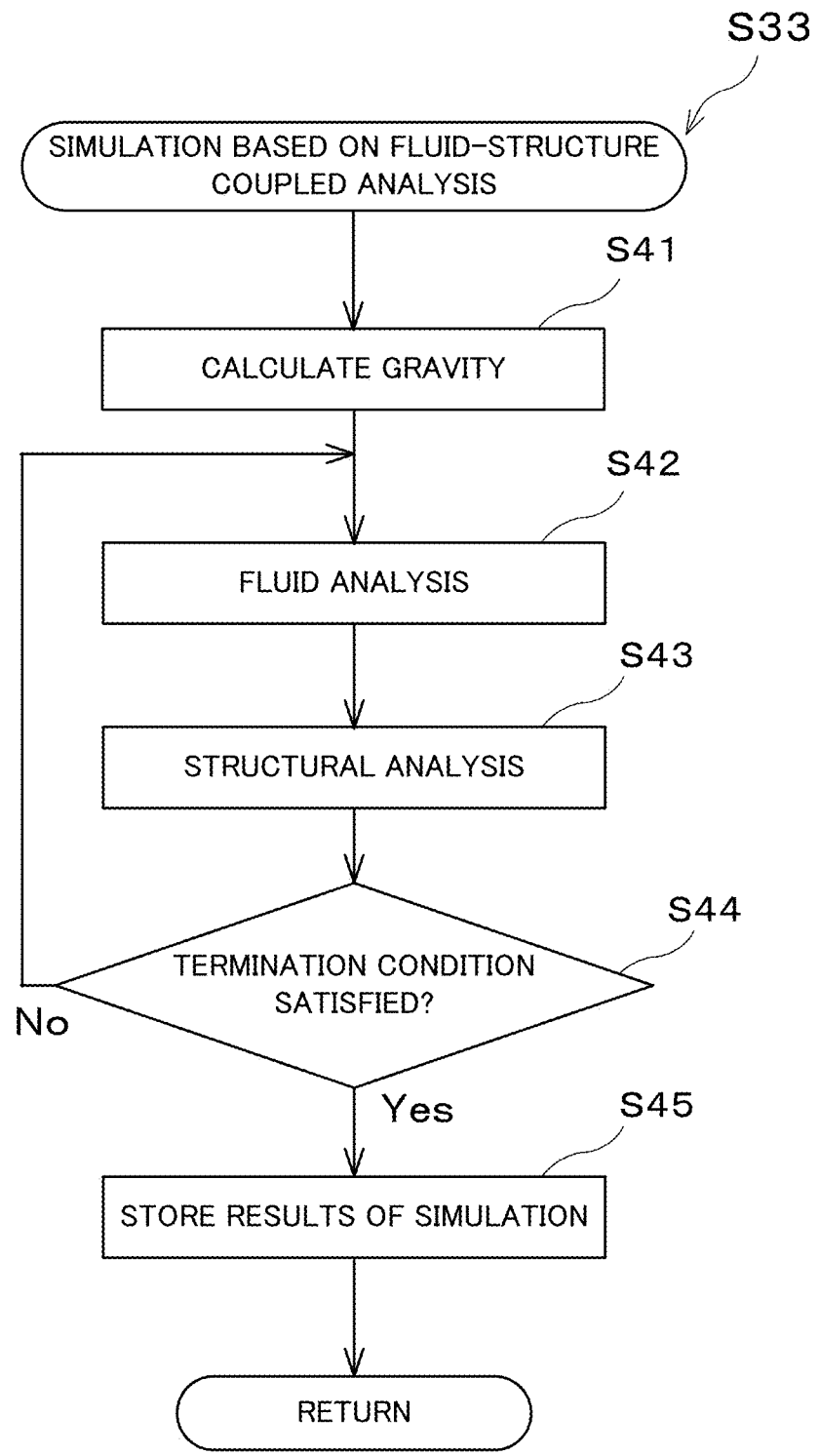
FIG. 20 is a flowchart illustrating a process of simulation based on the fluid-structure coupled analysis.

FIG. 20 illustrates the process of the simulation based on the fluid-structure coupled analysis in Step S33. The simulator 14 calculates the gravity and simulates deformed three-dimensional models of the surrounding tissues (Step S41). The deformed three-dimensional models of the upper airway and its surrounding tissues are illustrated in FIG. 13B.

Figure 21:
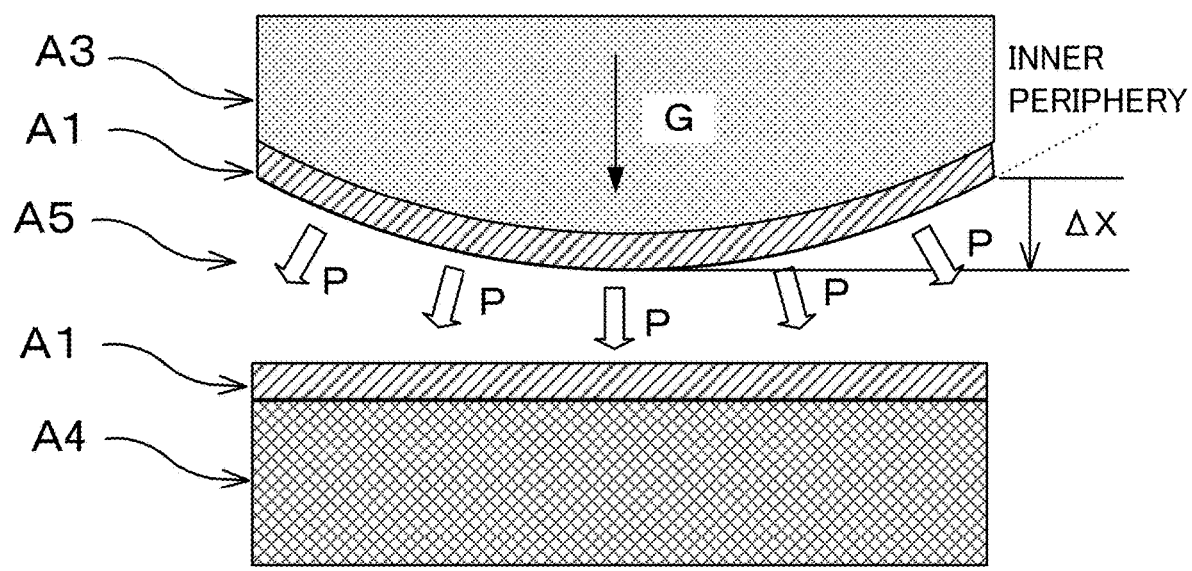
FIG. 21 is a schematic diagram illustrating forces applied on individual elements.

FIG. 21 is a schematic diagram illustrating the upper airway and its surrounding tissues when the subject lies in a supine position. As illustrated in FIG. 21, when the subject lies in a supine position, the upper airway A1 is located between the upper tongue A3 and the lower bone A4 in the vertical direction. The tongue A3 hangs down due to the gravity G and thereby deforms and narrows the upper airway A1 in comparison to when the subject is in an upright position.

Referring back to FIG. 20, the simulator 14 calculates the pressure P inside the upper airway through the fluid analysis of the fluid model A5 inside the upper airway A1 (Step S42). The simulator 14 also acquires a loading condition on the inner periphery (boundary) of the upper airway A1 on the basis of the pressure P (refer to FIG. 21) calculated through the fluid analysis.

The simulator 14 calculates, for example, a displacement (for example, Δx in FIG. 21) of the inner periphery of the upper airway in a state in which the gravity G and the pressure P are balanced, through the structural analysis of the upper airway A1 and its surrounding tissues using the loading condition as the boundary condition (Step S43). The simulator 14 updates the three-dimensional models of the upper airway and its surrounding tissues on the basis of the displacement of the inner periphery calculated through the structural analysis.

The simulator 14 determines whether the termination condition is satisfied (Step S44). The termination condition can be defined as convergence of the loading condition and the displacement of the inner periphery in the allowable ranges.

If the termination condition is not satisfied (Step S44; No), the simulator 14 executes fluid analysis on the basis of the displacement of the inner periphery calculated through the structural analysis (Step S42). Steps S42, S43, and S44 are repeated in this manner. The repetition of the steps causes the loading condition (pressure P) and the displacement (Δx) of the inner periphery converge to certain values.

The negative pressure P occurs inside the upper airway during inhalation of a respiratory cycle, as illustrated in FIG. 21. This negative pressure P further narrows the upper airway and displaces the boundary of the upper airway. This simulation involves repetition of the fluid analysis using the fluid model of the air inside the upper airway and the structural analysis using the models of the upper airway and its surrounding tissues. The simulation acquires a collection of the final loading condition (pressure P) and the final displacement (Δx) of the inner periphery after convergence in the allowable range for each boundary element as the pressure and displacement distributions inside the upper airway.

If the termination condition is satisfied as the pressure P inside the upper airway and the gravity G are balanced (Step S44; Yes), the simulator 14 terminates the simulation and stores the results of simulation into the storage 10 (Step S45). The simulation based on the fluid-structure coupled analysis is thus terminated. The simulation result data 26 stored in the storage 10 includes the pressure distribution inside the upper airway, the displacement distribution inside the upper airway, and the deformed three-dimensional models of the tissues surrounding the upper airway at the time of satisfaction of the termination condition.

Referring back to FIG. 19, the outputter 15 displays the results of simulation (Step S34). The display 35 thus displays the information, such as the pressure distribution and the flow velocity distribution inside the upper airway and the deformed three-dimensional models of the tissues surrounding the upper airway.

The simulation results displayed on the outputter 15 show the information, such as the pressure distribution inside the upper airway of the subject and deformation of the upper airway and its surrounding tissues during respiration. This information contributes to detection of a narrowed portion in the upper airway. The detection of a narrowed portion in the upper airway facilitates specification of a site responsible for sleep apnea syndrome.

As described above, the outputter 15 can display not only the pressure distribution inside the upper airway or the displacement distribution inside the upper airway but also the deformed three-dimensional models of the tissues surrounding the upper airway. This configuration can achieve more exact specification of a site of the surrounding tissues that narrows the upper airway.

Figure 22:
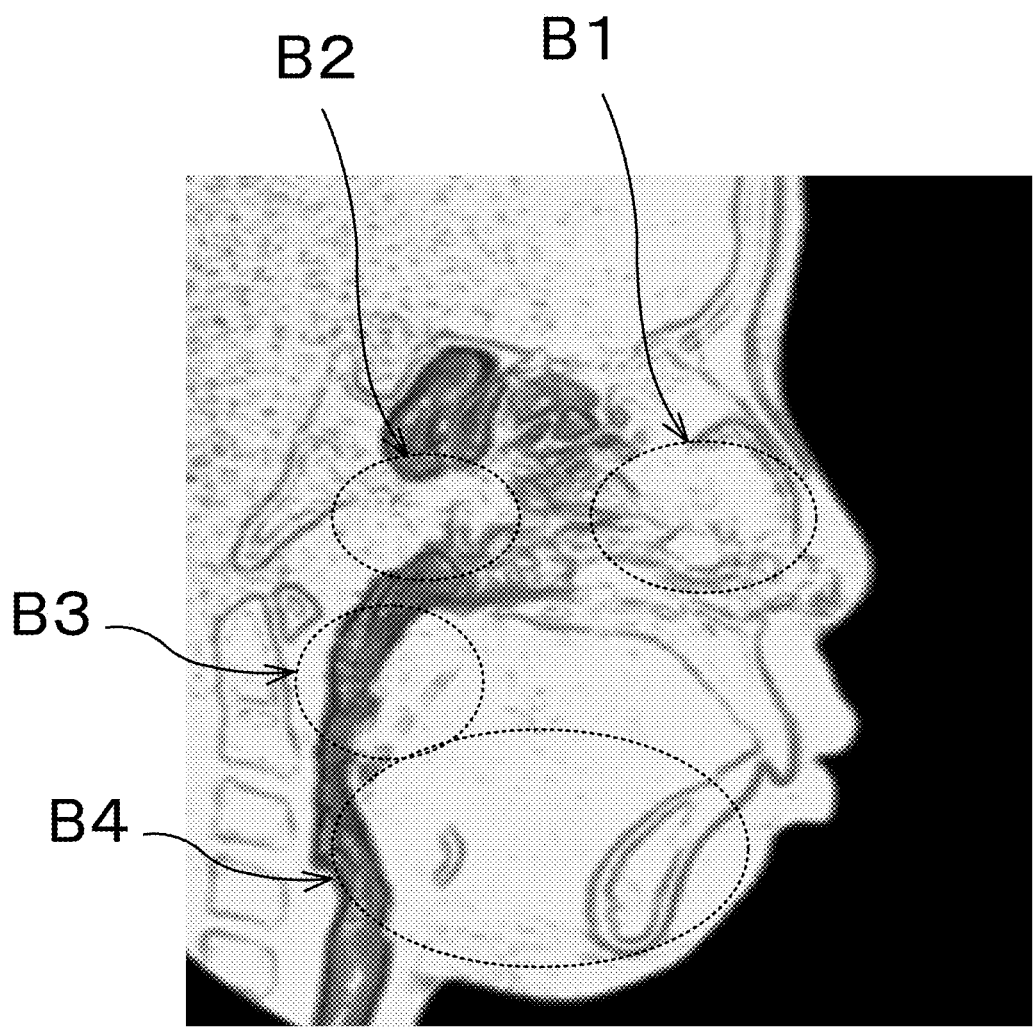
FIG. 22 illustrates sites to be treated.

For example, with reference to FIG. 22, in the case of extremely high pressure in the site B1, the cause of sleep apnea syndrome is likely to be a nasal cavity, which has nasal obstruction or nasal catarrh. The nose should be treated in this case.

In the case of extremely high pressure in the site B2, the cause of sleep apnea syndrome is likely to be an adenoid. The adenoid should be removed as an appropriate treatment procedure in this case.

In the case of extremely high pressure in the site B3, the cause of sleep apnea syndrome is likely to be a palatine tonsil. The soft palate should be treated in this case.

In the case of extremely high pressure in the site B4, the cause of sleep apnea syndrome is likely to be the jaw. The lower jaw should be treated in this case. A typical treatment procedure is correction of occlusion of the upper and lower teeth or weight reduction in this case.

The cause of sleep apnea syndrome is not always a single site. Two or more of the sites B1 to B4 illustrated in FIG. 22 can be responsible for sleep apnea syndrome. The simulation based on the fluid-structure coupled analysis according to the embodiment facilitates specification of two or more sites responsible for sleep apnea syndrome.

As described in detail above, the simulation based on the fluid-structure coupled analysis is executed using not only the three-dimensional model of the upper airway but also the three-dimensional models of the surrounding tissues of the upper airway according to the embodiment. This analysis can calculate deformation of the upper airway and its surrounding tissues as well as the air flow inside the upper airway according to respiration. The analysis can thus simulate the actual conditions of the upper airway and its surrounding tissues in a sleeping state, thereby enabling more exact specification of a site responsible for respiratory diseases. The analysis therefore more certainly leads to a preferable therapeutic outcome for respiratory diseases.

According to the embodiment, the nasal cavity model 50 can be generated of which the nasal cavity resistance 51 is equal to the actually-measured nasal cavity resistance 52. The resulting nasal cavity model 50 can therefore exactly simulate the nasal cavities of the subject. In addition, the three-dimensional model of the entire upper airway can be generated using the calibrated pixel extraction range. This model can faithfully simulate the actual conditions of the upper airway and its surrounding tissues in a sleeping state, thereby enabling more exact specification of a site responsible for respiratory diseases. The model therefore more certainly leads to a preferable therapeutic outcome for respiratory diseases.

The amount of increment or decrement of the second pixel density value CT2 depending on the difference between the nasal cavity resistances 51 and 52 may also be determined by a procedure other than the example illustrated in FIG. 10. The amount of increment or decrement may be larger or smaller than the amount in this example. Furthermore, the amount of increment or decrement of the second pixel density value CT2 may vary more or less rapidly depending on the difference between the nasal cavity resistances 51 and 52. Alternatively, the amount of increment or decrement of the second pixel density value CT2 may be constant.

Although only the second pixel density value CT2 is shifted in this embodiment, the first pixel density value CT1 may also be shifted. That is, the entire range of pixel density value of the pixels to be extracted may be shifted.

Embodiment 2

Embodiment 2 of the disclosure will now be described.

A diagnostic system according to Embodiment 2 of the disclosure is used in the planning of treatment for sleep apnea syndrome, which is a type of respiratory diseases.

Figure 23:
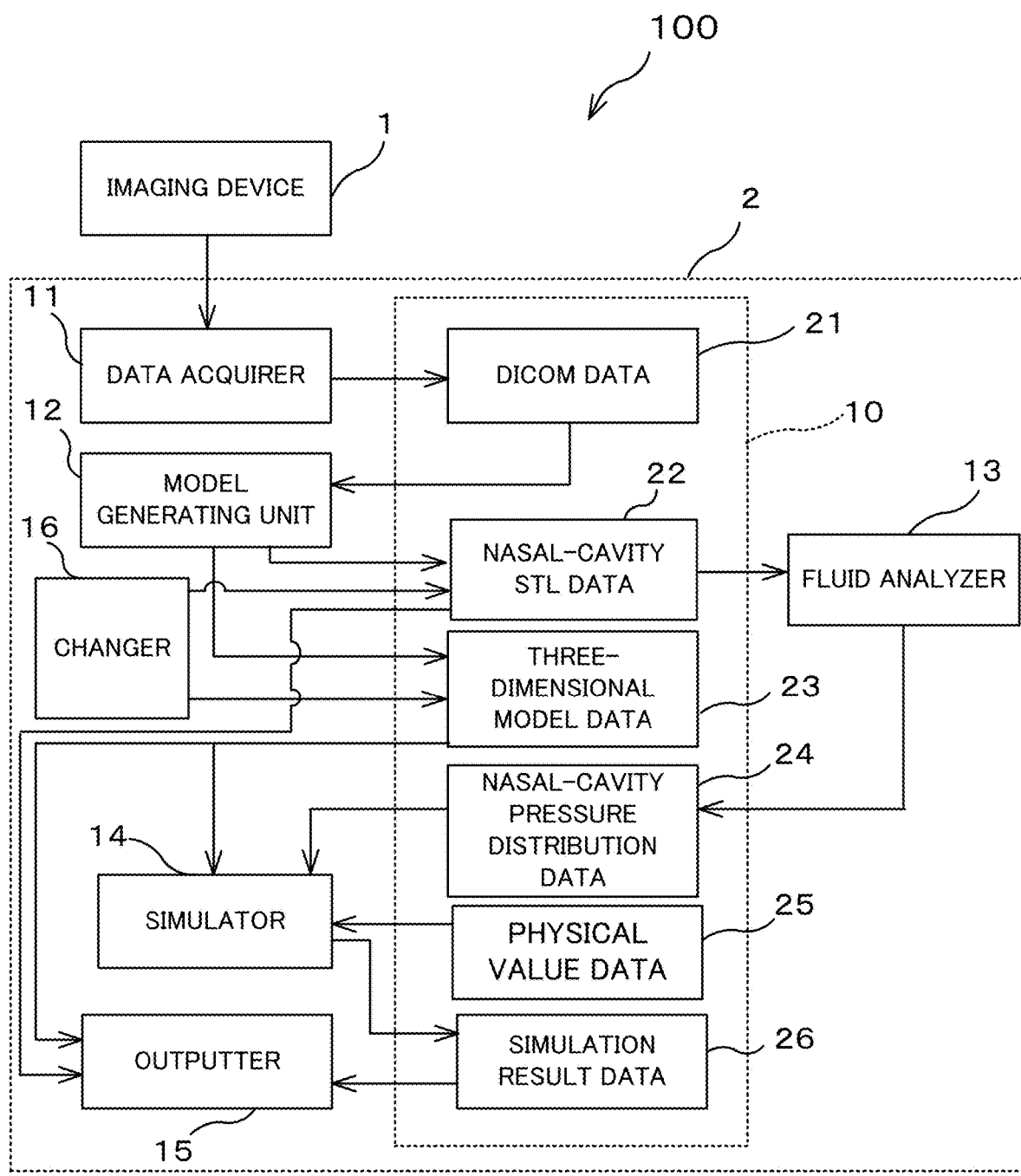
FIG. 23 is a block diagram illustrating a schematic configuration of a diagnostic system according to Embodiment 2 of the disclosure.

With reference to FIG. 23, the diagnostic system 100 according to this embodiment includes the outputter 15 capable of displaying the three-dimensional models of the upper airway and its surrounding tissues generated by the model generating unit 12, and differs from the diagnostic system 100 according to Embodiment 1 in that the computer 2 is further provided with a changer 16.

The outputter 15 displays the models of the upper airway and its surrounding tissues on the basis of the nasal-cavity STL data 22 and the three-dimensional model data 23 stored in the storage 10 in response to the input operation.

An operator manipulates the operation unit 34 (for example, by manipulation of the mouse) while watching the three-dimensional models of the upper airway and its surrounding tissues displayed on the outputter 15 to designate a specific region in the three-dimensional model. The operation is input through the operation unit 34 to the controller 31, so that the controller 31 conducts a process in accordance with the input operation. This function corresponds to the changer 16 illustrated in FIG. 23.

Figure 24:
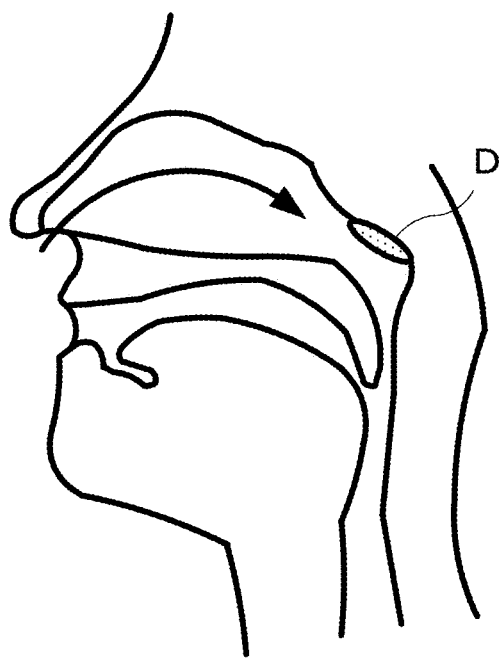
FIG. 24 is a schematic diagram illustrating an upper airway and its surrounding tissues before change.

For example, the region D illustrated in FIG. 24 is designated as the specific region through an operation input through the operation unit 34. In this case, the changer 16 changes the three-dimensional mesh models of the upper airway and its surrounding tissues by removing the designated region D in accordance with the operation input through the operation unit 34. The outputter 15 then displays the changed three-dimensional mesh models of the upper airway and its surrounding tissues. The changer 16 thus changes the three-dimensional mesh models of the upper airway and its surrounding tissues in accordance with the input operation.

Figure 25:
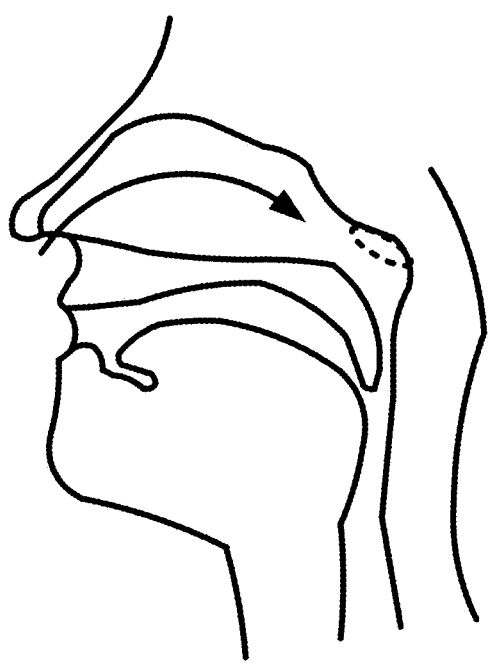
FIG. 25 is a schematic diagram illustrating the upper airway and its surrounding tissues after change.

FIG. 25 illustrates the upper airway and its surrounding tissues after removal of the designated region D. The changed three-dimensional models are stored into the storage 10 in the form of the three-dimensional model data 23. If the changed region D is located in the nasal cavity area, the STL data on the nasal cavity area after change is stored into the storage 10 in the form of the nasal-cavity STL data 22.

After completion of the change by the changer 16, the simulator 14 executes simulation based on the fluid-structure coupled analysis for the upper airway and its surrounding tissues according to respiration of the subject using the three-dimensional mesh models of the upper airway and its surrounding tissues, which are edited by the changer 16 and stored in the storage 10. The simulator 14 thereby calculates information on the air flow inside the upper airway and information on deformation of the upper airway. These results of simulation are stored into the storage 10 in the form of the simulation result data 26 and displayed on the outputter 15. The results show the ventilation condition of the upper airway after removal of the designated region D.

As described in detail above, the simulation based on the fluid-structure coupled analysis is executed using the three-dimensional models of the upper airway and its surrounding tissues changed by the changer 16 according to the embodiment. This simulation can obtain predictive information on the ventilation condition of the upper airway after treatment. The simulation can achieve prediction of the conditions of the upper airway and its surrounding tissues in a sleeping state after surgery and thus contribute to appropriate planning of treatment before surgery, such as determination of the optimal amount of tissues to be removed. The simulation therefore more certainly leads to a preferable therapeutic outcome for respiratory diseases.

The cause of sleep apnea syndrome is not always a single site, as described above. The diagnostic system 100 according to the embodiment can exactly specify multiple responsible sites by analyzing a variation in the ventilation condition of the upper airway through the simulation while changing the three-dimensional models of the individual tissues suspected as responsible sites.

The above embodiments can be directed to any subject. The diagnosis and treatment for sleep apnea syndrome can be applied to both children and adults. The sleep apnea syndrome seriously affects the growth of children. The incidence rate of sleep apnea syndrome in children with Down syndrome is reported to be higher than 50%. The exact specification of a site responsible for sleep apnea syndrome can thus bring numerous benefits to the society. The exact specification of a site responsible for sleep apnea syndrome leads to a significant reduction in medical expenses and preventive measures for serious incidents, resulting in lower economic losses and safer society.

Although the fluid-structure coupled analysis is executed by a weak coupling method (time difference method) in the above embodiments, the fluid-structure coupled analysis may also be executed by, for example, a strong coupling method (monolithic method) to strictly and contemporarily solve the governing equations of fluid and structure. That is, the simulation based on the fluid-structure coupled analysis can use various methods other than the above-mentioned method.

Although the three-dimensional models of the upper airway and its surrounding tissues and the fluid model of the air inside the upper airway are generated by a finite element method in the above embodiments, this example should not be construed as limiting the disclosure. For example, the three-dimensional models of the upper airway and its surrounding tissues and the fluid model of the air inside the upper airway may also be generated by a numerical analysis method, such as a finite difference method, a boundary element method, or a finite volume method, other than the finite element method.

Embodiment 3

Figure 26:
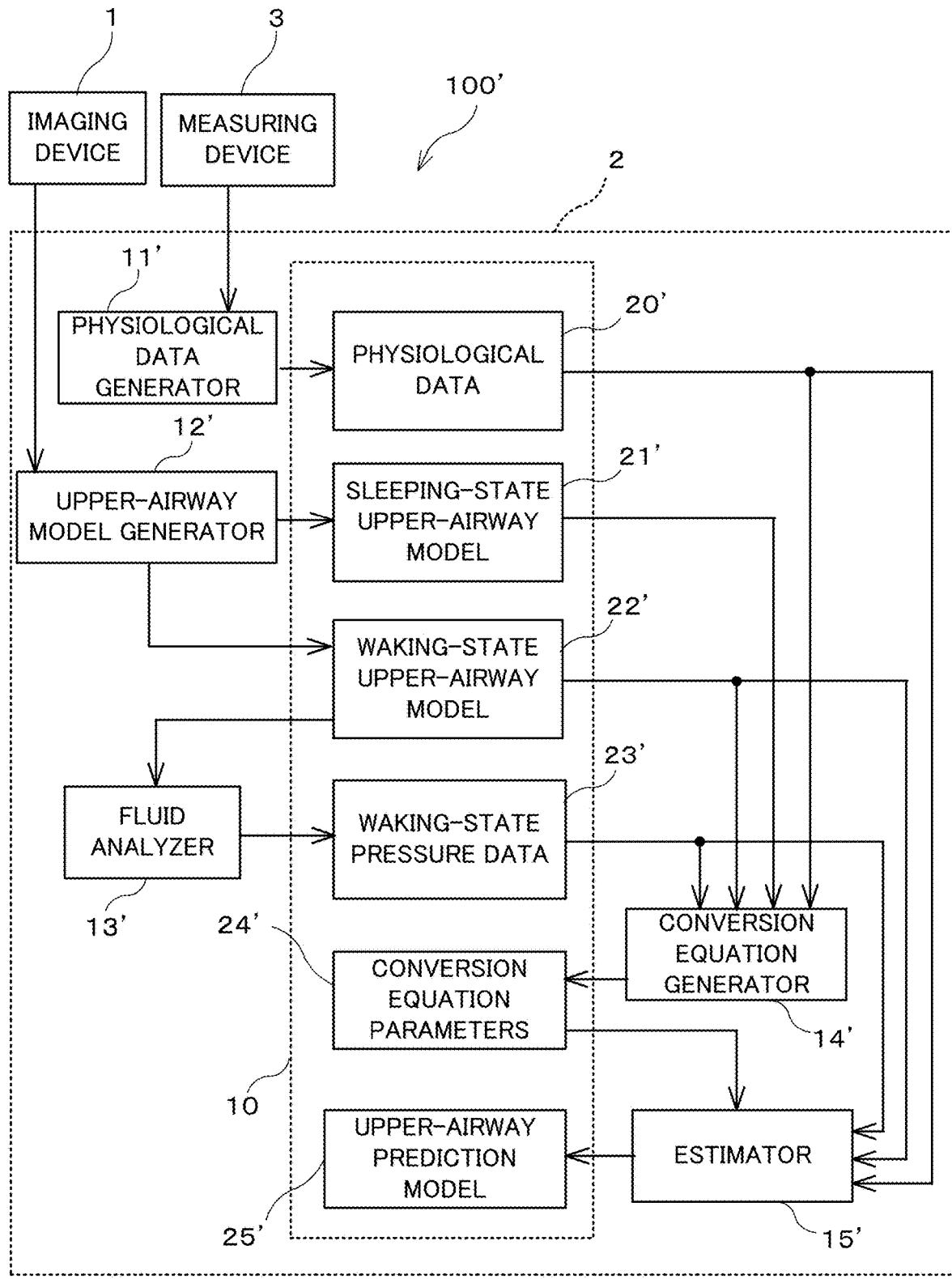
FIG. 26 is a block diagram illustrating a schematic configuration of an airway deformation prediction system according to Embodiment of the disclosure.

An airway deformation prediction system 100' according to Embodiment 3 illustrated in FIG. 26 includes all the components of the diagnostic system 100 illustrated in FIG. 1. The airway deformation prediction system 100' is used to predict the ventilation condition of the upper airway of a human body (subject) in a sleeping state on a computer for specifying a site responsible for sleep apnea syndrome. The airway deformation prediction system 100' predicts deformation of the upper airway in a sleeping state on the basis of measurement data on the upper airway of the subject obtained by a device, such as an X-ray computer tomography (CT) device, so as to simulate the ventilation condition of the upper airway of the subject. This embodiment is directed mainly to deformation of the pharynx and larynx.

As illustrated in FIG. 26, the airway deformation prediction system 100' includes an imaging device 1, a computer 2, and a measuring device 3. The imaging device 1 is connected to the computer 2 via a communication network. The communication network enables the imaging device 1 and the computer 2 to transmit and receive data to and from each other.

The imaging device 1 is an X-ray CT device. The imaging device 1 captures a three-dimensional X-ray CT image of the maxillofacial area of the subject. The imaging device 1 is identical to the imaging device 1 according to the above embodiments.

The computer 2 predicts deformation of the upper airway of the subject in a sleeping state on the basis of the three-dimensional X-ray CT image data contained in the received DICOM data. This prediction is conducted by an optimization procedure, such as regression analysis.

The computer 2 has the same hardware configuration as the computer 2 illustrated in FIG. 2. The functions of the individual components of the computer 2 illustrated in FIG. 26 are achieved by execution of the program 39 illustrated in FIG. 2 using hardware resources, such as the controller 31, the main memory 32, the external memory 33, the operation unit 34, the display 35, and the communicator 36.

The computer 2 having the hardware configuration illustrated in FIG. 2 has a functional configuration including the storage 10, a physiological data generator 11', an upper-airway model generator 12', a fluid analyzer 13', a conversion equation generator 14', and an estimator 15', as illustrated in FIG. 26.

The storage 10 corresponds to the external memory 33 illustrated in FIG. 2 of the hardware configuration illustrated in FIG. 2. The storage 10 stores various types of data. Examples of the data stored in the storage 10 include physiological data 20', a sleeping-state upper-airway model 21', a waking-state upper-airway model 22', waking-state pressure data 23', conversion equation parameters 24', and an upper-airway prediction model 25'.

The physiological data generator 11' corresponds to the controller 31 and the communicator 36 of the hardware configuration illustrated in FIG. 2. The physiological data generator 11' receives input of various data on the subject measured by the measuring device 3. Examples of the various data on the subject include data on the shape (for example, weight and height), a respiration condition in a sleeping state, a blood pressure, and a blood oxygen level of the subject. Based on the received data, the physiological data generator 11' generates various physiological data related to deformation of the upper airway in a sleeping state. The generated data for multiple subjects is stored into the storage 10 in the form of the physiological data 20'.

The upper-airway model generator 12' receives the three-dimensional X-ray CT image data (DICOM data) on the maxillofacial area transmitted from the imaging device 1. The upper-airway model generator 12' generates various data on the upper airway on the basis of the received DICOM data and stores the generated data into the storage 10.

Figure 31:
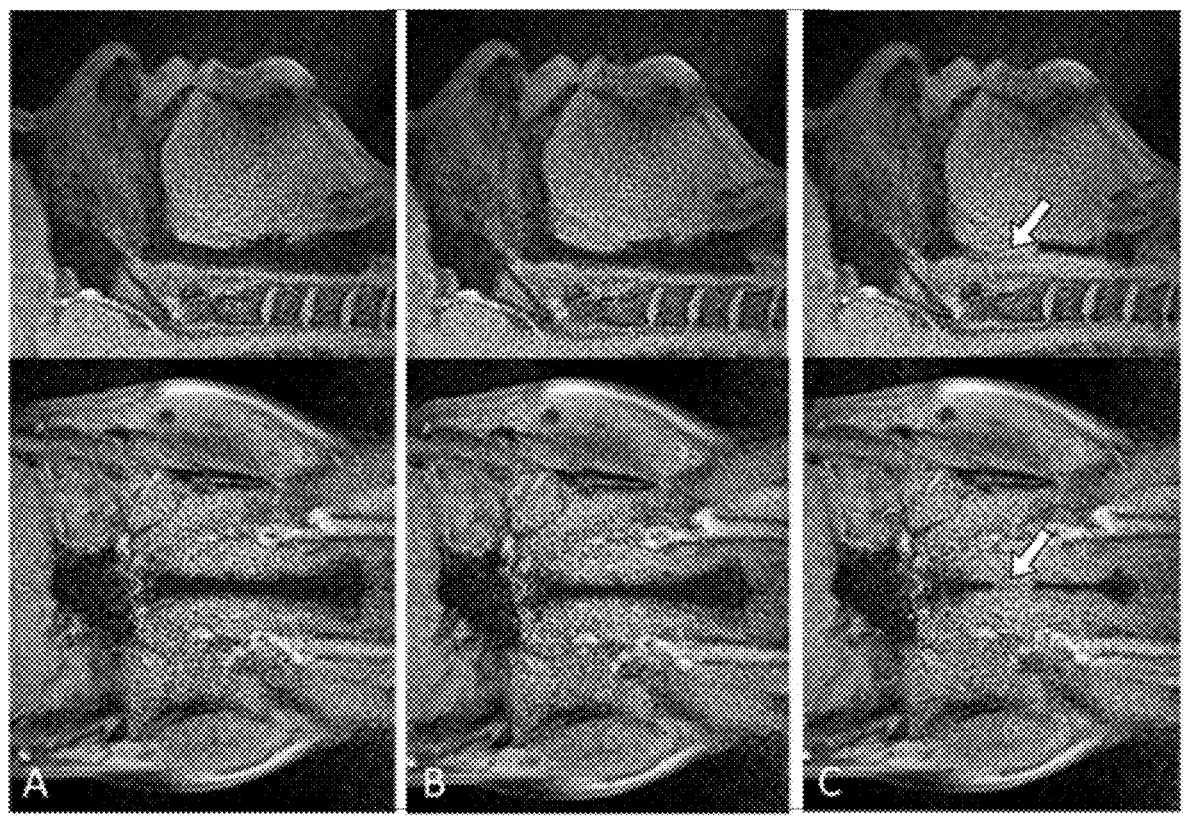
FIG. 31 illustrates CT images of the maxillofacial area of a subject captured in a waking state, a sleeping state, and with an obstructed airway in a sleeping state.
Figure 32A:
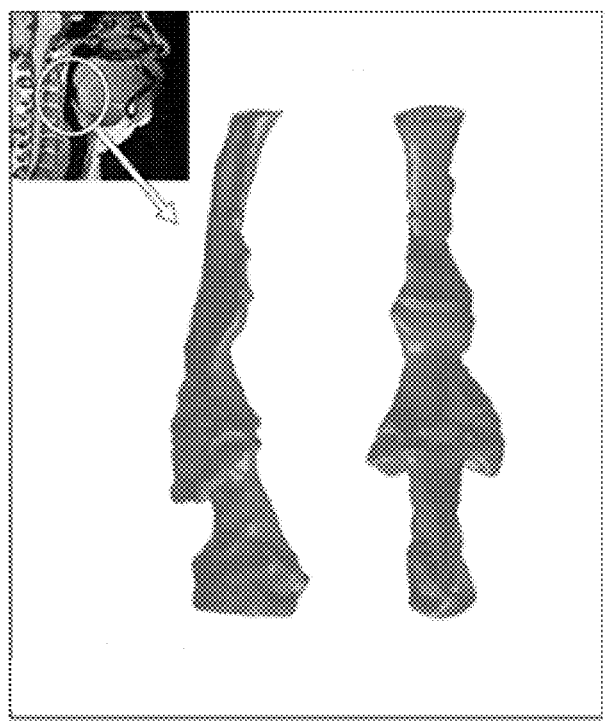
FIG. 32A illustrates an image of a three-dimensional model of an upper airway in a waking state.
Figure 32B:
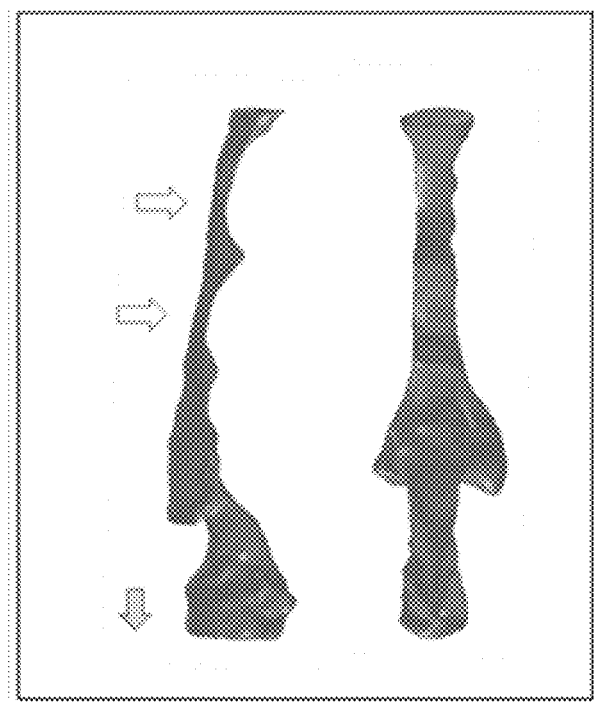
FIG. 32B illustrates an image of a three-dimensional model of the upper airway in a sleeping state.

The upper-airway model generator 12' stores three-dimensional models of upper airways (for example, refer to FIG. 32A), which are generated from the DICOM data (for example, refer to the section (A) of FIG. 31) captured while subjects are in waking states, into the storage 10 in the form of the waking-state upper-airway models 22'. In contrast, the upper-airway model generator 12' stores three-dimensional models of the upper airways (for example, refer to FIG. 32B), which are generated from the DICOM data (for example, refer to the sections (B) and (C) of FIG. 31) captured while the subjects are in sleeping states, into the storage 10 in the form of the sleeping-state upper-airway models 21'. The storage 10 stores the waking-state upper-airway models 22' and the sleeping-state upper-airway models 21' of multiple subjects sufficient for statistical calculation.

Figure 33A:
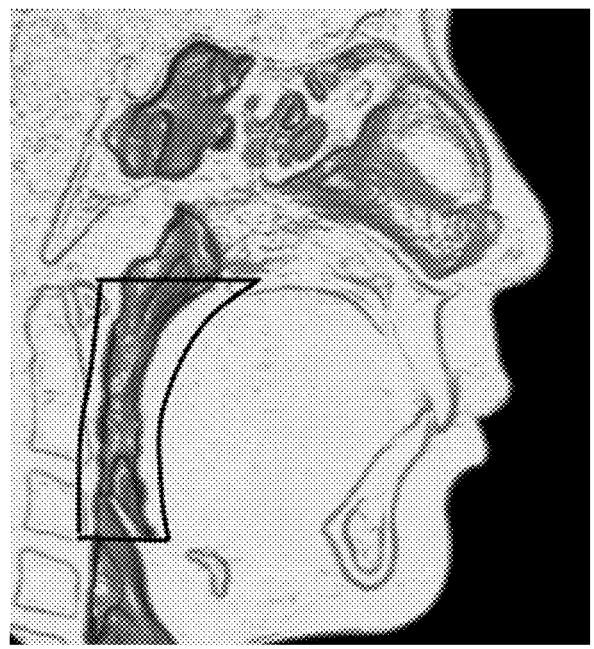
FIG. 33A illustrates the position of the upper airway in the maxillofacial area of a subject.
Figure 33B:
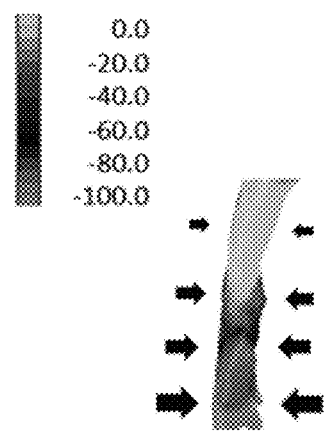
FIG. 33B illustrates a pressure distribution in an upper airway.

The fluid analyzer 13' calculates pressure data inside the upper airway (for example, refer to FIGS. 33A and 33B) through fluid analysis using each of the waking-state upper-airway models 22'. The calculated pressure data is stored into the storage 10 in the form of the waking-state pressure data 23'. The waking-state pressure data 23' is generated and stored for each of the subjects modeled in the waking-state upper-airway models 22'.

The conversion equation generator 14' receives input of the physiological data 20', the sleeping-state upper-airway models 21', the waking-state upper-airway models 22', and the waking-state pressure data 23'. The conversion equation generator 14' generates conversion equations that convert location information on a specific site of the upper airway in a waking state into location information on the specific site in a sleeping state, using the three-dimensional models of the upper airways of the multiple subjects in waking states and the three-dimensional models of the upper airways of the subjects in sleeping states. The comparison between the sections (A) and (C) of FIG. 31 or FIGS. 32A and 32B reveals that the upper airway of a certain subject has different shapes between in a waking state and in a sleeping state. This difference is reflected in the conversion equations generated by the conversion equation generator 14'.

The following description focuses on the conversion equations. The position coordinates of a specific site of the upper airway in a waking state is defined as (Xpre, Ypre, Zpre), and the position coordinates of the specific site in a sleeping state is defined as (Xpost, Ypost, Zpost). The pressure applied to the specific site of the upper airway in a waking state is defined as P. The relationship between the position coordinates (Xpre, Ypre, Zpre) of the specific site of the upper airway in a waking state and the position coordinates (Xpost, Ypost, Zpost) of the specific site in a sleeping state is represented by the three linear combination equations below:

$$X\text{post} = X\text{pre} + a \times P + b \times \text{AHI} + c \times \text{BMI} + \ldots + d \quad (1)$$

$$Y\text{post} = Y\text{pre} + e \times P + f \times \text{AHI} + g \times \text{BMI} + \ldots + h \quad (2)$$

$$Z\text{post} = Z\text{pre} + i \times P + j \times \text{AHI} + k \times \text{BMI} + \ldots + l \quad (3)$$

where a to l indicate the coefficients of the individual terms.

AHI indicates an apnea hypopnea index. The apnea means a symptom of interruption of respiration for at least ten seconds in a sleeping state. The number of occurrence of apnea per hour is called an apnea index (AI). The hypopnea means a symptom of a respiratory ventilation rate of 50% or less for at least ten seconds. The number of occurrence of hypopnea per hour is called a hypopnea index (HI). The sum of the numbers of occurrence of apnea and hypopnea per hour in a sleeping state is called an apnea hypopnea index (AHI).

BMI indicates a body mass index calculated by the relationship between the weight and height of a human to show the level of obesity.

The conversion equation generator 14' executes regression analysis by assigning the position coordinates (Xpre, Ypre, Zpre) of the specific site of the upper airway in waking states, the position coordinates (Xpost, Ypost, Zpost) of the specific site in sleeping states, the AHIs, and the BMIs for multiple subjects to the equations (1) to (3), to thereby calculate coefficients a to l that can achieve the minimum remainder between the predicted position coordinates in sleeping states and the actually-measured position coordinates (Xpost, Ypost, Zpost). The calculated coefficients a to l are stored into the storage 10 in the form of the conversion equation parameters 24'.

The estimator 15' assigns a waking-state upper-airway model 22' of a new subject to the generated conversion equations (1) to (3) (conversion equations containing the coefficients in the form of the conversion equation parameters 24') and thus generates the upper-airway prediction model 25' of this subject in a sleeping state. If the generated upper-airway prediction model 25' demonstrates a narrowed or collapsed portion in the upper airway, this portion is suspected to be responsible for sleep apnea syndrome.

Figure 27:
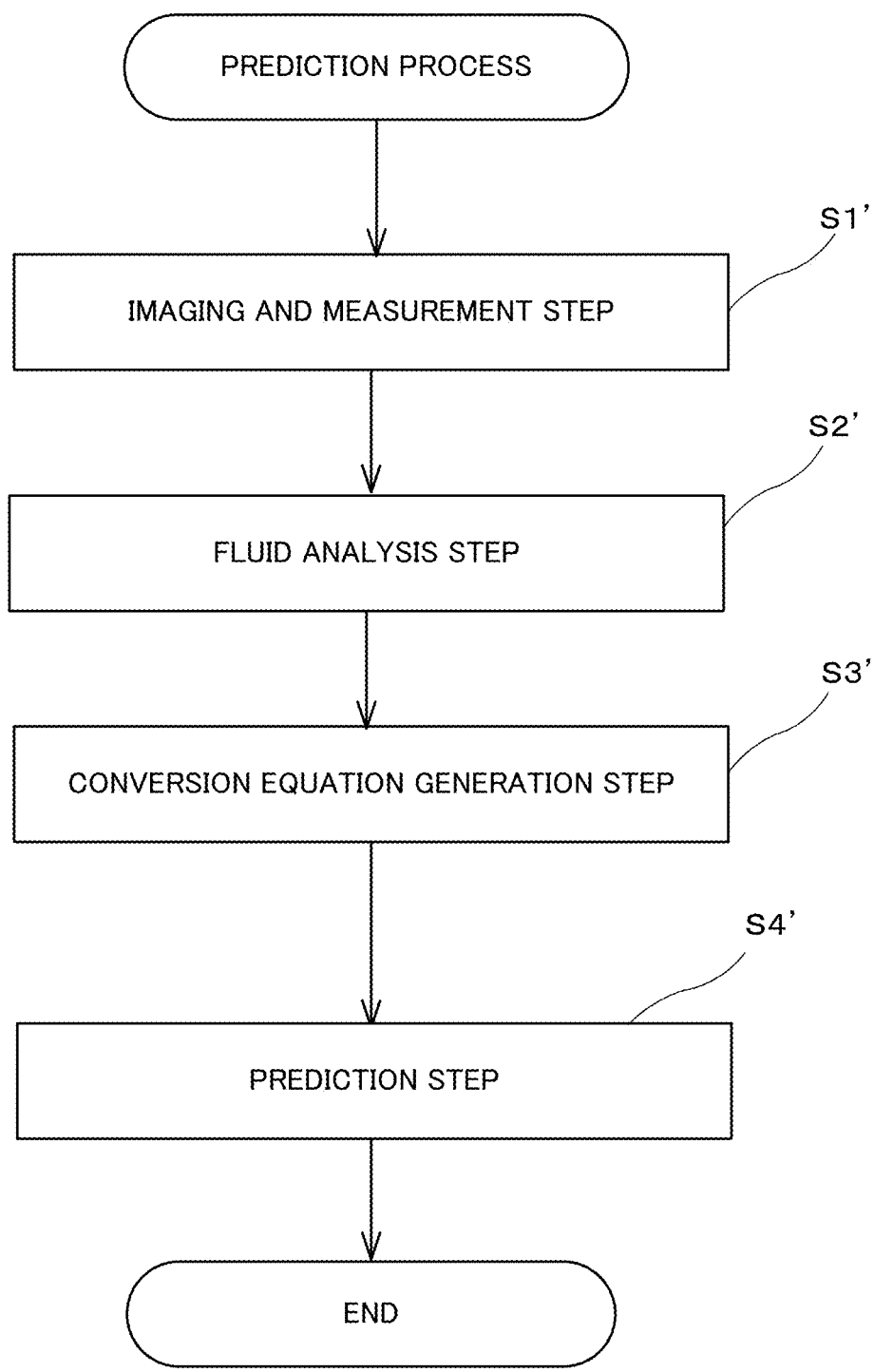
FIG. 27 is a flowchart illustrating a process (prediction process) for predicting airway deformation in the airway deformation prediction system.

The process of predicting airway deformation in the airway deformation prediction system 100' will now be explained. With reference to FIG. 27, first, the imaging device 1 captures the DICOM data on the subject, and the measuring device 3 measures the physiological data 20' on the subject in an imaging and measurement step (Step S1'). Accordingly, the DICOM data (refer to the sections (A) and (B) of FIG. 31) on the maxillofacial area of the subject is transmitted from the imaging device 1 to the computer 2, and the physiological data 20' on the subject is transmitted from the measuring device 3 to the computer 2.

The upper-airway model generator 12' generates the sleeping-state upper-airway model 21' and the waking-state upper-airway model 22' on the basis of the DICOM data, and stores the generated models into the storage 10. The physiological data generator 11' calculates the values (for example, AHI and BMI) defined in the individual terms of the conversion equations in accordance with the results of measurement by the measuring device 3, and stores the calculated values into the storage 10 in the form of the physiological data 20'.

The computer 2 then executes fluid analysis in a fluid analysis step (Step S2'). Specifically, the fluid analyzer 13' generates the waking-state pressure data 23'(refer to FIG. 33B) through the fluid analysis using the waking-state upper-airway model 22', and stores the generated data into the storage 10.

Figure 28:
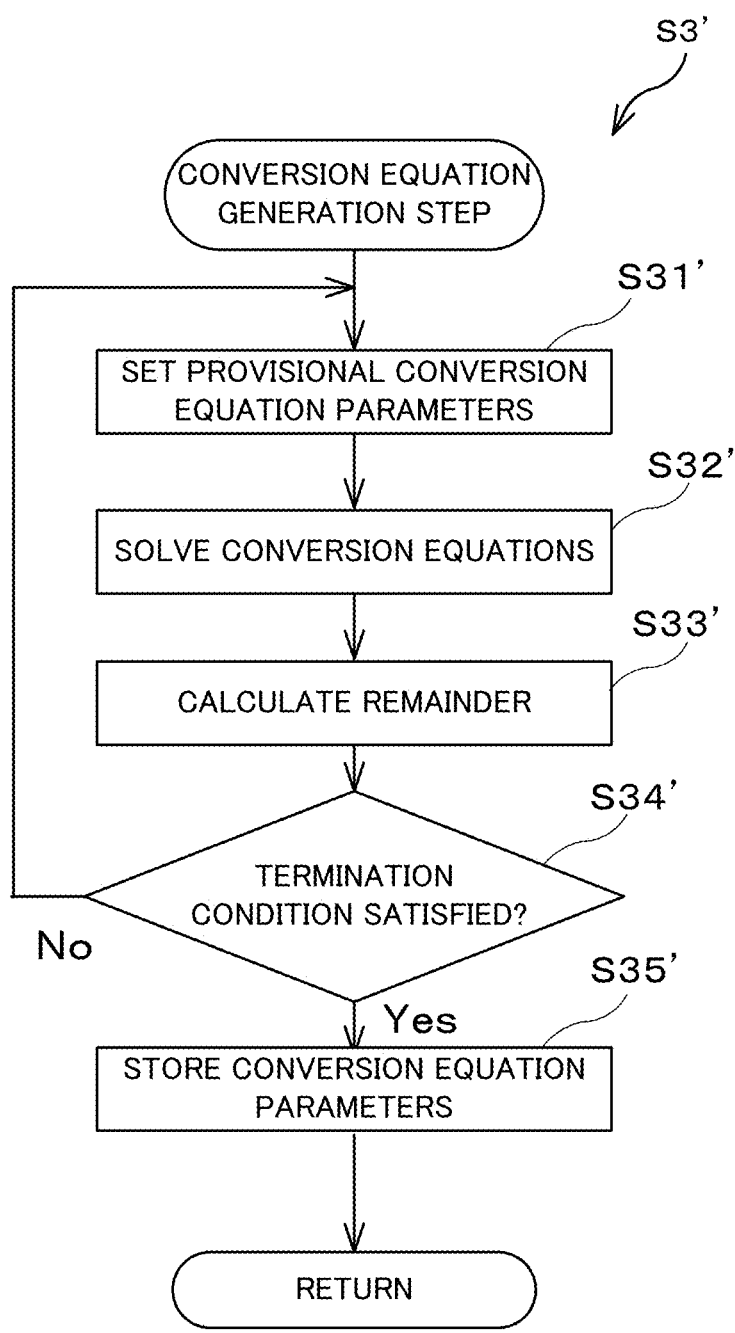
FIG. 28 is a flowchart illustrating a subroutine of the conversion equation generation step in FIG. 27.

Thereafter, the computer 2 generates the conversion equations in a conversion equation generation step (Step S3'). Specifically, with reference to FIG. 28, the conversion equation generator 14' assigns provisional values to the coefficients a to l of the conversion equations, that is, sets provisional conversion equation parameters (Step S31'). The conversion equation generator 14' then solves the conversion equations by assigning the values, such as the position coordinates (Xpre, Ypre, Zpre) of the specific site of the upper airway in a waking state, the pressure P at the specific site, the AHI, and the BMI (Step S32'). The conversion equation generator 14' then calculates the remainder between the position coordinates calculated from the conversion equations and the actually-measured position coordinates in a sleeping state (Step S33').

The conversion equation generator 14' determines whether the termination condition is satisfied (Step S34'). The termination condition is defined as, for example, the calculated remainder within an allowable range.

If determining that the termination condition is not satisfied (Step S34'; No), the conversion equation generator 14' sets provisional conversion equation parameters (that is, assigns different values to the coefficients a to l) (Step S31'), solves the conversion equations (Step S32'), calculates the remainder (Step S33'), and determines satisfaction of the termination condition (Step S34').

The steps S31', S32', S33', and S34' are repeated in this manner until the termination condition becomes satisfied, to find the optimal conversion equation parameters (coefficients a to l) that provide the remainder satisfying the termination condition.

If the termination condition is satisfied (Step S34'; Yes), the conversion equation generator 14' stores the outstanding coefficients (conversion equation parameters 24') of the conversion equations into the storage 10 (Step S35').

Figure 29:
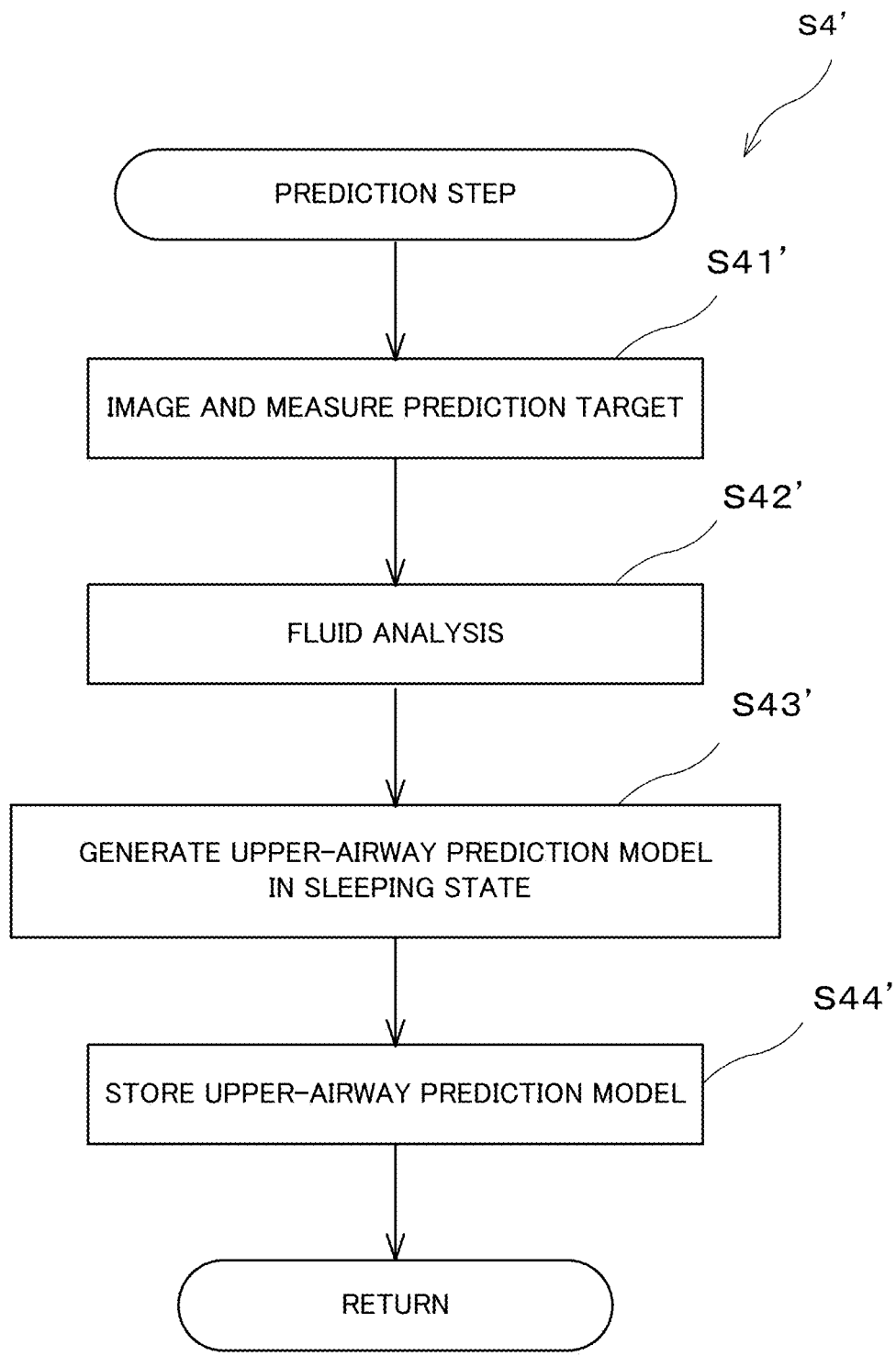
FIG. 29 is a flowchart illustrating a subroutine of the prediction step in FIG. 27.

Referring back to FIG. 27, the computer 2 then conducts a prediction step (Step S4'). Specifically, with reference to FIG. 29, first, the imaging device 1 captures an image of a subject (prediction target) in a waking state, the measuring device 3 measures the physiological data 20' on the subject, and the results of imaging and measurement are transmitted to the computer 2 (Step S41'). Based on the received results, the upper-airway model generator 12' generates the waking-state upper-airway model 22' and stores the generated model into the storage 10. The physiological data generator 11' generates the physiological data 20' and stores the generated data into the storage 10.

The fluid analyzer 13' then generates the waking-state pressure data 23' (refer to FIG. 33B) through the fluid analysis using the waking-state upper-airway model 22', and stores the generated data into the storage 10 (Step S42').

Thereafter, the estimator 15' reads and defines the conversion equation parameters 24' as the coefficients a to l of the conversion equations. The estimator 15' calculates the position coordinates (Xpost, Ypost, Zpost) in a sleeping state by assigning the position coordinates (Xpre, Ypre, Zpre) in the waking-state upper-airway model 22', to thereby generate the upper-airway prediction model 25' (Step S43'). The estimator 15' then stores the upper-airway prediction model 25' into the storage 10 (Step S44'). In this step, the upper-airway prediction model 25' may be displayed on the display 35 if required. The process is thus terminated.

Figure 34:
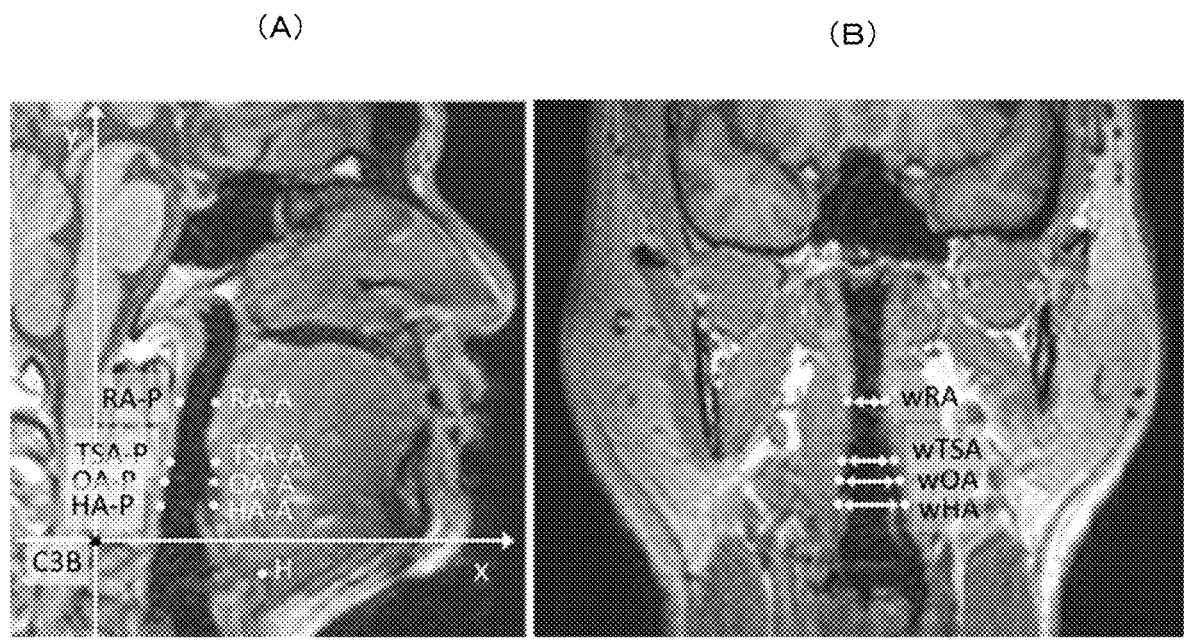
FIG. 34 illustrates individual sites in an upper airway and the intervals therebetween.

Although the shape of the entire upper airway is predicted in this embodiment, this example should not be construed as limiting the disclosure. The prediction may be focused only on a variation in the position coordinates of a specific site of the upper airway in a sleeping state. Examples of the specific site include the sites RA-P, RA-A, TSA-P, TSA-A, OA-P, OA-A, HA-P, and HA-A illustrated in the section (A) of FIG. 34. Each of the lengths wRA, wTSA, wOA, and wHA illustrated in the section (B) of FIG. 34 indicates the interval between two corresponding specific sites, that is, the width of the airway at these sites.

The displayed upper-airway prediction model 25' demonstrates the shape of the upper airway of the subject in a sleeping state. This information contributes to detection of a narrowed portion in the upper airway. The detection of a narrowed portion in the upper airway facilitates specification of a site responsible for sleep apnea syndrome.

Figure 30:
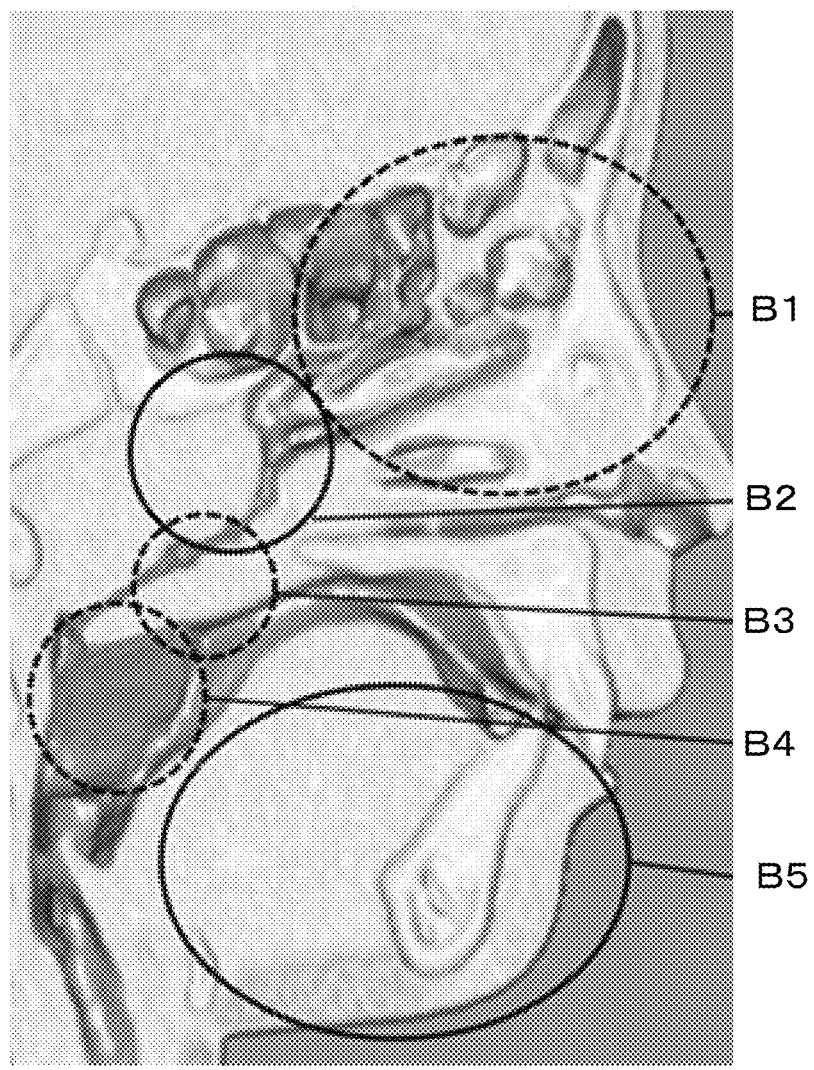
FIG. 30 illustrates exemplary sites responsible for sleep apnea syndrome.

For example, with reference to FIG. 30, if the site B1 (the mucous membrane of the nose) has inflammation, an appropriate treatment procedure is to suppress the inflammation by medication, for example.

If the site B2 (the back part of the nose) has a swelling, an appropriate treatment procedure is to remove the swelling by surgery.

If the site B3 (the back part of the throat) is thickened, an appropriate treatment procedure is permanent installation of a machine, such as a CPAP device.

If the site B4 (the tonsil) has a swelling, an appropriate treatment procedure is to remove the tonsil by surgery.

If the lower part of the upper airway is collapsed or narrowed, the site B5 (the lower jaw) is suspected as a responsible site. The lower jaw should be treated in this case. A typical treatment procedure is correction of occlusion of the upper and lower teeth, weight reduction, surgery for shifting the lower jaw forward, or use of a mouthpiece.

The cause of sleep apnea syndrome is not always a single site. Two or more of the sites B1 to B5 illustrated in FIG. 30 may be responsible sites. The prediction of deformation of the upper airway in a sleeping state according to the embodiment facilitates specification of two or more sites responsible for sleep apnea syndrome.

As described in detail above, this embodiment can achieve statistical prediction of the shape of the upper airway of each subject in a sleeping state from the shape of the upper airway in a waking state, using the conversion equations estimated by the optimization procedure from the waking-state upper-airway models 22' and the sleeping-state upper-airway models 21' of multiple subjects. The embodiment can thus determine the shape of the upper airway in a sleeping state and achieve exact specification of a site responsible for obstructive sleep apnea syndrome (OSAS).

Although the conversion equations have the terms of the body mass index in the embodiment, this example should not be construed as limiting the disclosure. For example, the body mass index may be replaced with other index indicating the level of obesity (for example, the height/weight, body fat percentage, Rohrer index, or obesity index).

Although the imaging device 1 is an X-ray CT device in the above embodiments, this example should not be construed as limiting the disclosure. The imaging device 1 may also be a magnetic resonance imaging (MRI) device or an ultrasonic diagnostic device. Alternatively, a single piece of three-dimensional image data may be generated from multiple pieces of three-dimensional image data obtained by an X-ray CT device, an MRI device, and an ultrasonic diagnostic device, and may be used to generate three-dimensional models of the tissues.

Although the coefficients of the conversion equations are optimized by the regression analysis in the above embodiment, this example should not be construed as limiting the disclosure. The optimal parameters of the conversion equations may also be acquired by other optimization procedure, such as genetic algorithms. In this case, the optimization procedure may be conducted excluding data significantly deviated from the standard.

Although the above embodiments are directed to diagnosis and treatment for sleep apnea syndrome, this example should not be construed as limiting the disclosure. The system may also be applied to diagnosis and treatment for other respiratory diseases associated with the shape of the upper airway. The system may also be applied to specification of a cause of other symptoms, such as high blood pressure.

The illustrated hardware and software configurations of the computer 2 are mere examples and may be altered and modified in any manner.

The central part that performs the functions of the computer 2, which includes the controller 31, the main memory 32, the external memory 33, the operation unit 34, the display 35, the communicator 36, and the internal bus 30 may be achieved by an ordinal computer system without a dedicated system. For example, a computer program for performing the above functions may be stored in a non-transitory computer-readable recording medium (for example, a flexible disk, a CD-ROM, or a DVD-ROM) for distribution, and may be installed in a computer to configure the computer 2 that performs the above functions. Alternatively, this computer program may be stored in a storage device included in a server on a communication network, such as the Internet, and may be downloaded into an ordinal computer system to configure the computer 2.

In the case in which the functions of the computer 2 are achieved by sharing of an operating system (OS) and an application program or by cooperation of the OS and the application program, only the application program may be stored in a non-transitory recording medium or a storage device.

The computer program may be distributed via a communication network while being superimposed on a carrier wave. For example, the computer program may be posted on a bulletin board system (BBS) on a communication network and may be distributed via the network. Alternatively, the computer program may be configured to perform the above functions by being activated and executed under the control of an OS like other application programs.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2017-38358, filed on Mar. 1, 2017, the entire disclosure of which is incorporated by reference herein.

INDUSTRIAL APPLICABILITY

The disclosure can be applied to specification of a site responsible for diseases in an upper airway, such as obstructive sleep apnea syndrome (OSAS).

REFERENCE SIGNS LIST

1 Imaging device
2 Computer
3 Measuring device
10 Storage
11 Data acquirer
12 Model generating unit
13 Fluid analyzer
14 Simulator
15 Outputter
16 Changer
21 DICOM data
22 Nasal-cavity STL data
23 Three-dimensional model data
24 Nasal-cavity pressure distribution data
25 Physical value data
26 Simulation result data
30 Internal bus
31 Controller
32 Main memory 33 External memory
34 Operation unit
35 Display
36 Communicator
39 Program
41 Nasal-cavity model generator
42 Nasal-cavity resistance calculator
43 Adjuster
50 Nasal cavity model
51, 52 Nasal cavity resistance
100 Diagnostic system
11' Physiological data generator
12' Upper-airway model generator
13' Fluid analyzer
14' Conversion equation generator
15' Estimator
20' Physiological data
21' Sleeping-state upper-airway model
22' Waking-state upper-airway model
23' Waking-state pressure data
24' Conversion equation parameter
25' Upper-airway prediction model
100' Airway deformation prediction system

The invention claimed is:

1. A model generating device comprising:
a nasal-cavity model generator configured to:
extract pixels from three-dimensional image data on a nasal cavity of a subject, the extracted pixels having pixel density values within a range defined between a first pixel density value and a second pixel density value larger than the first pixel density value, the first pixel density value being approximate to a pixel density value of air, and
generate a nasal cavity model based on the three-dimensional image data composed of the extracted pixels, the nasal cavity model being a three-dimensional model of the nasal cavity;
a nasal-cavity resistance calculator configured to calculate a nasal cavity resistance through fluid analysis using the nasal cavity model generated by the nasal-cavity model generator; and
an adjuster configured to adjust at least the second pixel density value for the pixels to be extracted for generation of the nasal cavity model by the nasal cavity model generator such that the nasal cavity resistance calculated by the nasal-cavity resistance calculator is equal to an actually-measured nasal cavity resistance, wherein the second pixel density value is adjusted by:
incrementing the second pixel density value when the nasal cavity resistance calculated by the nasal-cavity resistance calculator is larger than the actually-measured nasal cavity resistance, or
decrementing the second pixel density value if the nasal cavity resistance calculated by the nasal-cavity resistance calculator is smaller than the actually-measured nasal cavity resistance.

2. The model generating device according to claim 1, wherein the adjuster decreases an amount of increment or decrement of the second pixel density value as the nasal cavity resistance calculated by the nasal-cavity resistance calculator approaches the actually-measured nasal cavity resistance.

3. The model generating device according to claim 1, further comprising an upper-airway model generator configured to extract pixels from three-dimensional image data on a maxillofacial area of the subject and generate a three-dimensional model of a tissue of an upper airway based on three-dimensional image data composed of the extracted pixels, the pixels having the pixel density values within the specific range adjusted by the adjuster.

4. A system for predicting airway deformation in a sleeping state, the system comprising:
the model generating device according to claim 1;
a conversion equation generator configured to generate conversion equations by an optimization procedure using three-dimensional models of upper airways of a plurality of subjects in waking states and three-dimensional models of the upper airways of a plurality of subjects in sleeping states, the conversion equations converting location information on a specific site of an upper airway in a waking state into location information on the specific site in a sleeping state; and
an estimator configured to estimate location information on the specific site of the upper airway of the subject in a sleeping state by assigning location information on the specific site of the upper airway of the subject in a waking state to the generated conversion equations.

5. The system for predicting airway deformation in a sleeping state according to claim 4, wherein the conversion equation generator generates coefficients of the conversion equations through regression analysis using location information on specific sites of the upper airways of the subjects in waking states obtained from the three-dimensional models of the upper airways in waking states and location information on the specific sites in sleeping states obtained from the three-dimensional models of the upper airways in sleeping states.

6. The system for predicting airway deformation in a sleeping state according to claim 5, wherein the conversion equations are linear combination equations comprising terms of position coordinates of the specific site of the upper airway in a waking state and terms of a pressure applied to the specific site, the pressure being obtained through fluid analysis using a three-dimensional model of the upper airway in a waking state.

7. The system for predicting airway deformation in a sleeping state according to claim 6, wherein the conversion equations are linear combination equations further comprising terms of an apnea hypopnea index.

8. The system for predicting airway deformation in a sleeping state according to claim 6, wherein the conversion equations are linear combination equations further comprising terms of an index related to a level of obesity of the subject.

9. A model generating method comprising:
a nasal-cavity model generation step of:
extracting pixels having pixel density values from three-dimensional image data on a nasal cavity of a subject, the extracted pixels having pixel density values within a range defined between a first pixel density value and a second pixel density value larger than the first pixel density value, the first pixel density value being approximate to a pixel density value of air, and
generating a nasal cavity model based on the three-dimensional image data composed of the extracted pixels, the nasal cavity model being a three-dimensional model of the nasal cavity;
a simulation step of calculating a nasal cavity resistance through fluid analysis using the nasal cavity model generated in the nasal-cavity model generation step; and
an adjustment step of adjusting at least the second pixel density value for the pixels to be extracted for generation of the nasal cavity model in the nasal-cavity model generation step until the nasal cavity resistance calculated in the simulation step becomes equal to a nasal cavity resistance actually measured with a nasal-cavity draft gauge, wherein the second pixel density value is adjusted by:
  incrementing the second pixel density value when the nasal cavity resistance calculated by the nasal-cavity resistance calculator is larger than the actually-measured nasal cavity resistance, or
  decrementing the second pixel density value if the nasal cavity resistance calculated by the nasal-cavity resistance calculator is smaller than the actually-measured nasal cavity resistance.

10. A method for predicting airway deformation in a sleeping state, the method comprising:
  a nasal-cavity model generation step of:
    extracting pixels having pixel density values within a specific range from three-dimensional image data on a nasal cavity of a subject, the extracted pixels having pixel density values within a range defined between a first pixel density value and a second pixel density value larger than the first pixel density value, the first pixel density value being approximate to a pixel density value of air, and
    generating a nasal cavity model based on the three-dimensional image data composed of the extracted pixels, the nasal cavity model being a three-dimensional model of the nasal cavity;
  a simulation step of calculating a nasal cavity resistance through fluid analysis using the nasal cavity model generated in the nasal-cavity model generation step;
  an adjustment step of adjusting at least the second pixel density value for the pixels to be extracted for generation of the nasal cavity model in the nasal-cavity model generation step until the nasal cavity resistance calculated in the simulation step becomes equal to a nasal cavity resistance actually measured with a nasal-cavity draft gauge, wherein the second pixel density value is adjusted by:
    incrementing the second pixel density value when the nasal cavity resistance calculated by the nasal-cavity resistance calculator is larger than the actually-measured nasal cavity resistance, or
    decrementing the second pixel density value if the nasal cavity resistance calculated by the nasal-cavity resistance calculator is smaller than the actually-measured nasal cavity resistance;
  a conversion equation generation step of generating conversion equations by an optimization procedure using three-dimensional models of upper airways of a plurality of subjects in waking states and three-dimensional models of the upper airways of a plurality of subjects in sleeping states, the conversion equations converting location information on a specific site of an upper airway in a waking state into location information on the specific site in a sleeping state; and
  an estimation step of estimating location information on the specific site of the upper airway of the subject in a sleeping state by assigning location information on the specific site of the upper airway of the subject in a waking state to the generated conversion equations.

* * * * *